United States Patent
Anderberg et al.

(10) Patent No.: US 10,935,548 B2
(45) Date of Patent: *Mar. 2, 2021

(54) METHODS FOR DIAGNOSIS AND PROGNOSIS OF RENAL INJURY AND RENAL FAILURE USING INSULIN-LIKE GROWTH FACTOR-BINDING PROTEIN 7 AND METALLOPROTEINASE INHIBITOR 2

(71) Applicant: ASTUTE MEDICAL, INC., San Diego, CA (US)

(72) Inventors: Joseph Anderberg, Encinitas, CA (US); Jeff Gray, Solana Beach, CA (US); Paul McPherson, Encinitas, CA (US); Kevin Nakamura, Cardiff by the Sea, CA (US); James Patrick Kampf, San Diego, CA (US)

(73) Assignee: Astute Medical, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/363,724

(22) PCT Filed: Dec. 7, 2012

(86) PCT No.: PCT/US2012/068498
§ 371 (c)(1),
(2) Date: Jun. 6, 2014

(87) PCT Pub. No.: WO2013/086359
PCT Pub. Date: Jun. 13, 2013

(65) Prior Publication Data
US 2014/0377777 A1    Dec. 25, 2014

Related U.S. Application Data

(60) Provisional application No. 61/593,561, filed on Feb. 1, 2012, provisional application No. 61/568,447, filed on Dec. 8, 2011.

(51) Int. Cl.
G01N 33/53    (2006.01)
G01N 33/545    (2006.01)
G01N 33/68    (2006.01)

(52) U.S. Cl.
CPC ....... G01N 33/545 (2013.01); G01N 33/6893 (2013.01); *G01N 2333/8146* (2013.01); *G01N 2800/26* (2013.01); *G01N 2800/347* (2013.01); *G01N 2800/52* (2013.01); *G01N 2800/56* (2013.01)

(58) Field of Classification Search
CPC ............ G01N 33/545; G01N 33/6893; G01N 2333/8146; G01N 2800/56; G01N 2800/26; G01N 2800/52; G01N 2800/347
See application file for complete search history.

(56) References Cited

U.S. PATENT DOCUMENTS

| | | |
|---|---|---|
| 5,118,614 A | 6/1992 | Rybák et al. |
| 5,324,634 A | 6/1994 | Zucker |
| 5,480,792 A | 1/1996 | Buechler et al. |
| 5,525,524 A | 6/1996 | Buechler et al. |
| 5,571,698 A | 11/1996 | Ladner et al. |
| 5,631,171 A | 5/1997 | Sandstrom et al. |
| 5,679,526 A | 10/1997 | Buechler et al. |
| 5,824,799 A | 10/1998 | Buechler et al. |
| 5,851,776 A | 12/1998 | Valkirs |
| 5,885,527 A | 3/1999 | Buechler |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler |
| 6,057,098 A | 5/2000 | Buechler et al. |

(Continued)

FOREIGN PATENT DOCUMENTS

| | | |
|---|---|---|
| CN | 1791797 | 6/2006 |
| EP | 0828159 | 3/1998 |

(Continued)

OTHER PUBLICATIONS

Siew, J Am Soc Nephrol 22: 810-820, 2011.*
Stampher et al., Circulation 2004, 1909:IV3-IV-5.*
Caron et al. (Experimental Cell Research. 301:105-116, published 2005).*
Constantin et al., J.Crit Care2010 vol. 25:176.*
Devrajan et al, J Am Soc Nephrol 2006;vol. 17:1503-1520.*
Altom et al (Laboratory Robotics and automation vol. 2, issue 3, 139-46, see Abstract.*
Keightley 1989; Laboratory Practice vol. 38, issue 10, p. 56-5, see Abstract.*

(Continued)

*Primary Examiner* — Carmencita M Belei
(74) *Attorney, Agent, or Firm* — Womble Bond Dickinson (US) LLP

(57) ABSTRACT

The present invention relates to methods and compositions for monitoring, diagnosis, prognosis, and determination of treatment regimens in sepsis patients. In particular, the invention relates to using assays that detect one or more biomarkers selected from the group consisting of Insulin-like growth factor-binding protein 7, Beta-2-glycoprotein 1, Metalloproteinase inhibitor 2, Alpha-1 Antitrypsin, Leukocyte elastase, Serum Amyloid P Component, C-X-C motif chemokine 6, Immunoglobulin A, Immunoglobulin G subclass I, C-C motif chemokine 24, Neutrophil collagenase, Cathepsin D, C-X-C motif chemokine 13, Involucrin, Interleukin-6 receptor subunit beta, Hepatocyte Growth Factor, CXCL-1, -2, -3, Immunoglobulin G subclass II, Metalloproteinase inhibitor 4, C-C motif chemokine 18, Matrilysin, C-X-C motif chemokine 11, and Antileukoproteinase as diagnostic and prognostic biomarker assays of renal injury in the sepsis patient.

21 Claims, No Drawings

Specification includes a Sequence Listing.

(56) References Cited

U.S. PATENT DOCUMENTS

| | | | |
|---|---|---|---|
| 6,113,855 A | 9/2000 | Buechler et al. | |
| 6,140,045 A | 10/2000 | Wohlstadter et al. | |
| 6,143,576 A | 11/2000 | Buechler | |
| 6,218,122 B1 | 4/2001 | Friend et al. | |
| 6,664,385 B1 | 12/2003 | Sanicola-Nadel et al. | |
| 6,784,154 B2 | 8/2004 | Westenfelder | |
| 6,861,404 B1 | 3/2005 | Cohen et al. | |
| 6,941,172 B2 | 9/2005 | Nachum | |
| 7,138,230 B2 | 11/2006 | Hu et al. | |
| 7,141,382 B1 | 11/2006 | Parikh et al. | |
| 7,235,358 B2 | 6/2007 | Wohlgemuth et al. | |
| 7,608,413 B1 | 10/2009 | Joseloff et al. | |
| 7,623,910 B2 | 11/2009 | Couderc et al. | |
| 7,662,578 B2 | 2/2010 | Devarajan | |
| 7,833,699 B2 | 11/2010 | Locht et al. | |
| 7,981,684 B2 | 7/2011 | Levin et al. | |
| 7,998,744 B2 | 8/2011 | Stevenson et al. | |
| 8,008,008 B2 | 8/2011 | Parr et al. | |
| 8,071,293 B2 | 12/2011 | High et al. | |
| 8,080,394 B2 | 12/2011 | Levy et al. | |
| 8,241,861 B1 | 8/2012 | Heinecke et al. | |
| 8,778,615 B2 | 7/2014 | Anderberg et al. | |
| 8,993,250 B2 | 3/2015 | Anderberg et al. | |
| 9,029,093 B2 | 5/2015 | Anderberg et al. | |
| 9,057,735 B2 | 6/2015 | Anderberg et al. | |
| 9,229,010 B2 | 1/2016 | Anderberg et al. | |
| 9,360,488 B2 | 6/2016 | Anderberg et al. | |
| 9,459,261 B2 | 10/2016 | Anderberg et al. | |
| 9,696,322 B2 | 7/2017 | Anderberg et al. | |
| 9,784,750 B2 | 10/2017 | Anderberg et al. | |
| 9,822,172 B2 | 11/2017 | Vijayendran et al. | |
| 9,879,091 B2 | 1/2018 | Vijayendran et al. | |
| 10,300,108 B2 | 5/2019 | McPherson et al. | |
| 2002/0012906 A1 | 1/2002 | Comper | |
| 2002/0055627 A1 | 5/2002 | Rosen et al. | |
| 2003/0003588 A1 | 1/2003 | Comper | |
| 2003/0186308 A1* | 10/2003 | Young | C07K 14/4743 435/6.14 |
| 2004/0053309 A1 | 3/2004 | Holt et al. | |
| 2004/0106155 A1 | 6/2004 | Comper | |
| 2004/0253637 A1* | 12/2004 | Buechler | A61B 5/14546 435/7.1 |
| 2005/0002934 A1 | 1/2005 | Reed | |
| 2005/0048033 A1 | 3/2005 | Fraser et al. | |
| 2005/0084880 A1* | 4/2005 | Duman | C12Q 1/6883 435/6.16 |
| 2005/0112688 A1 | 5/2005 | Hu et al. | |
| 2005/0137481 A1 | 6/2005 | Sheard et al. | |
| 2005/0148029 A1 | 7/2005 | Buechler et al. | |
| 2005/0158801 A1 | 7/2005 | Hu et al. | |
| 2005/0256075 A1 | 11/2005 | Alitalo et al. | |
| 2005/0272101 A1 | 12/2005 | Devarajan et al. | |
| 2006/0003327 A1 | 1/2006 | Achiron et al. | |
| 2006/0057066 A1 | 3/2006 | Natsoulis et al. | |
| 2006/0088823 A1 | 4/2006 | Haab et al. | |
| 2006/0204951 A1 | 9/2006 | Folkman et al. | |
| 2006/0223077 A1 | 10/2006 | Ni et al. | |
| 2006/0240437 A1 | 10/2006 | Krolewski et al. | |
| 2006/0246485 A1 | 11/2006 | Sarwal et al. | |
| 2006/0257903 A1* | 11/2006 | Akil | C12Q 1/6883 435/6.16 |
| 2007/0031905 A1 | 2/2007 | Shariat | |
| 2007/0087387 A1 | 4/2007 | Devarajan et al. | |
| 2007/0093969 A1 | 4/2007 | Mendrick et al. | |
| 2007/0105142 A1 | 5/2007 | Wilhelm | |
| 2007/0112327 A1 | 5/2007 | Yun et al. | |
| 2007/0154897 A1 | 7/2007 | Yen et al. | |
| 2007/0184439 A1* | 8/2007 | Guilford et al. | 435/6 |
| 2007/0248989 A1 | 10/2007 | Devarajan | |
| 2007/0249002 A1* | 10/2007 | Hu | G01N 33/57442 435/7.92 |
| 2008/0014644 A1 | 1/2008 | Barasch et al. | |
| 2008/0038192 A1 | 2/2008 | Gervais | |
| 2008/0038269 A1 | 2/2008 | Susan | |
| 2008/0090304 A1 | 4/2008 | Barasch et al. | |
| 2008/0090759 A1 | 4/2008 | Kokenyesi et al. | |
| 2008/0133141 A1 | 6/2008 | Frost | |
| 2008/0153092 A1 | 6/2008 | Kienle et al. | |
| 2008/0166717 A1 | 7/2008 | Thorin | |
| 2008/0206794 A1 | 8/2008 | Hu et al. | |
| 2008/0254483 A1 | 10/2008 | Darbouret et al. | |
| 2008/0254485 A1 | 10/2008 | Valkirs et al. | |
| 2009/0004687 A1 | 1/2009 | Mansfield et al. | |
| 2009/0022730 A1 | 1/2009 | Raulf et al. | |
| 2009/0047689 A1 | 2/2009 | Kolman et al. | |
| 2009/0081713 A1 | 3/2009 | Klein et al. | |
| 2009/0088409 A1 | 4/2009 | Charlton | |
| 2009/0090856 A1 | 4/2009 | Grant et al. | 435/7.23 |
| 2009/0130693 A1* | 5/2009 | Bassi et al. | 435/7.23 |
| 2009/0148539 A1 | 6/2009 | Elias et al. | |
| 2009/0176656 A1 | 7/2009 | Halloran | |
| 2009/0179287 A1 | 7/2009 | Inaba | |
| 2009/0197287 A1 | 8/2009 | Hu et al. | |
| 2009/0203588 A1 | 8/2009 | Willman et al. | |
| 2009/0220526 A1 | 9/2009 | Hamid | |
| 2009/0258002 A1 | 10/2009 | Barrett et al. | |
| 2009/0298073 A1 | 12/2009 | Gerhold et al. | |
| 2009/0298106 A1 | 12/2009 | Hooper | |
| 2010/0022627 A1 | 1/2010 | Scherer | |
| 2010/0081148 A1 | 4/2010 | Singbartl et al. | |
| 2010/0190164 A1 | 7/2010 | Tammen et al. | |
| 2010/0240078 A1 | 9/2010 | Lee et al. | |
| 2010/0240081 A1 | 9/2010 | Rollinger et al. | |
| 2010/0267041 A1 | 10/2010 | Shuber et al. | |
| 2010/0267061 A1 | 10/2010 | Hsieh et al. | |
| 2011/0065608 A1 | 3/2011 | Labrie et al. | |
| 2011/0104726 A1 | 5/2011 | Valkirs et al. | |
| 2011/0174062 A1 | 7/2011 | Anderberg et al. | |
| 2011/0195429 A1 | 8/2011 | Anderberg et al. | |
| 2011/0201038 A1 | 8/2011 | Anderberg et al. | |
| 2011/0207161 A1 | 8/2011 | Anderberg et al. | |
| 2012/0156701 A1 | 6/2012 | Anderberg et al. | |
| 2012/0190044 A1 | 7/2012 | Anderberg et al. | |
| 2012/0190051 A1 | 7/2012 | Anderberg et al. | |
| 2012/0208717 A1 | 8/2012 | Hu et al. | |
| 2012/0283128 A1 | 11/2012 | Anderberg et al. | |
| 2012/0329071 A1 | 12/2012 | Chance et al. | |
| 2013/0035290 A1 | 2/2013 | Elias et al. | |
| 2013/0157881 A1 | 6/2013 | Anderberg et al. | |
| 2013/0210043 A1 | 8/2013 | Anderberg et al. | |
| 2014/0213477 A1 | 7/2014 | Anderberg et al. | |
| 2014/0315734 A1 | 10/2014 | Arnold et al. | |
| 2014/0323594 A1 | 10/2014 | Anderberg et al. | |
| 2014/0343600 A1 | 11/2014 | Leschinsky | |
| 2014/0356301 A1 | 12/2014 | Shyur et al. | |
| 2014/0377777 A1 | 12/2014 | Anderberg et al. | |
| 2016/0146832 A1 | 5/2016 | Chawla et al. | |
| 2017/0248613 A1 | 8/2017 | Anderberg et al. | |
| 2018/0074054 A1 | 3/2018 | McPherson et al. | |
| 2019/0263926 A1 | 8/2019 | McPherson et al. | |

FOREIGN PATENT DOCUMENTS

| | | |
|---|---|---|
| EP | 1777523 | 4/2007 |
| EP | 1905846 | 4/2008 |
| EP | 2261660 | 12/2010 |
| EP | 2480882 | 8/2012 |
| EP | 2513649 | 10/2012 |
| JP | 2003-081838 | 3/2003 |
| JP | 2014-234388 | 12/2014 |
| WO | WO 1998/055508 | 12/1998 |
| WO | WO 2000/037944 | 6/2000 |
| WO | WO 2003/054004 | 7/2003 |
| WO | WO 2003/075016 | 9/2003 |
| WO | WO 2004/005934 | 1/2004 |
| WO | WO 2004/059293 | 7/2004 |
| WO | WO 2005/087264 | 9/2005 |
| WO | WO 2006/010529 | 2/2006 |
| WO | WO 2006/072654 | 7/2006 |
| WO | WO 2006/083986 | 8/2006 |
| WO | WO 2007/013919 | 2/2007 |
| WO | WO 2007/041623 | 4/2007 |
| WO | WO 2007/082586 | 7/2007 |

(56) References Cited

FOREIGN PATENT DOCUMENTS

| | | |
|---|---|---|
| WO | WO 2007/124331 | 11/2007 |
| WO | WO 2007/124419 | 11/2007 |
| WO | WO 2008/060607 | 5/2008 |
| WO | 2008067065 A2 | 6/2008 |
| WO | WO 2008/084331 | 7/2008 |
| WO | WO 2008/089994 | 7/2008 |
| WO | WO 2008/104804 | 9/2008 |
| WO | WO 2008/116867 | 10/2008 |
| WO | WO 2008/122670 | 10/2008 |
| WO | WO 2008/154238 | 12/2008 |
| WO | WO 2009/038742 | 3/2009 |
| WO | WO 2009/062520 | 5/2009 |
| WO | WO 2010/025424 | 3/2010 |
| WO | WO 2010/025434 | 3/2010 |
| WO | WO 2010/045714 | 4/2010 |
| WO | WO 2010/048346 | 4/2010 |
| WO | WO 2010/048347 | 4/2010 |
| WO | WO2010048346 * | 4/2010 ............ G01N 33/48 |
| WO | WO 2010/054389 | 5/2010 |
| WO | WO 2010/091236 | 8/2010 |
| WO | WO 2010/111746 | 10/2010 |
| WO | WO 2010/128158 | 11/2010 |
| WO | 2011017614 | 2/2011 |
| WO | WO 2011/025917 | 3/2011 |
| WO | WO 2011/035323 | 3/2011 |
| WO | 2011075744 | 6/2011 |
| WO | 2011097539 A1 | 8/2011 |
| WO | WO 2011/106746 | 9/2011 |
| WO | WO 2011/162821 | 12/2011 |
| WO | WO 2013/043310 | 3/2013 |
| WO | WO 2013/086359 | 6/2013 |
| WO | WO 2014/113558 | 7/2014 |
| WO | WO 2014/197729 | 12/2014 |
| WO | WO 2015/021308 | 2/2015 |
| WO | WO 2015/069880 | 5/2015 |
| WO | WO 2015/084939 | 6/2015 |
| WO | WO 2016/164854 | 10/2016 |
| WO | WO 2017/060525 | 4/2017 |
| WO | WO 2017/214203 | 12/2017 |
| WO | WO 2018/081578 | 5/2018 |
| WO | WO 2018/145117 | 8/2018 |
| WO | WO 2018/187453 | 10/2018 |
| WO | WO 2018/208684 | 11/2018 |

OTHER PUBLICATIONS

Sheck et al 1992;Proc.Int.Symp.Lab.autom.Rob. p. 282-98, see Abstract.*
Ridker, "C-Reactive Protein: A Simple Test to Help Predict Risk of Heart Attack and Stroke", Circulation. 2003;108:e81-e85, doi:10.1161/01.CIR.0000093381.57779.67.
Christenson et al., "Standardization of Cardiac Troponin I Assays: Round Robin of Ten Candidate Reference Materials," Clinical Chemistry 47:3, 431-437 (2001).
Obuchowski et al., "ROC Curves in Clinical Chemistry: Uses, Misuses, and Possible Solutions", Clinical Chemistry 50:7, 1118-1125 (2004).
Sykes et al., Analytical Relationships Among Biosite, Bayer, and Roche Methods for BNP and NT-proBNP, Am J Clin Pathol 2005;123:584-590, DOI: 10.1309/F86FVEFDGX06DTUV.
Triage BNP Test Product Insert: Rapid Quantitative Test B-type Natriuretic Peptide, Alere Catalog # 98000XR, 2011, 28 pages.
The International Search Report and Written Opinion dated Feb. 8, 2013 in PCT/US2012/068498.
Bagshaw et al., Urinary biomarkers in septic acute kidney injury. Intensive Care Med. Jul. 2007;33(7):1285-1296.
Baso et al., Identification of candidate serum biomarkers for severe septic shock-associated kidney injury via microarray. Crit Care. 2011:15(6):R273.
Supplementary European Search Report issued in EP12854991 dated Jun. 23, 2015.
Lopez-Bermejo et al., Generation of Anti-Insulin-Like Growth Factor-Binding Protein-Related Protein 1 (IGFBP-rP1/MAC25) Monoclonal Antibodies and Immunoassay: Quantification of IGFBP-rP1 in Human Serum and Distribution in Human Fluids and Tissues. J Clin Endocrinol Metab. Jul. 2003;88(7):3401-3408.
Nejat et al., Urinary cystatin C is diagnostic of acute kidney injury and sepsis, and predicts mortality in the intensive care unit. Crit Care. 2010;14(3):R85.
Su et al., Diagnostic value of urine sTREM-1 for sepsis and relevant acute kidney injuries: a prospective study. Crit Care. 2011:15(5):R250.
Bagshaw et al., A multi-centre evaluation of the RIFLE criteria for early acute kidney injury in critically ill patients. Nephrol Dial Transplant. Apr. 2008;23(4):1203-1210.
Bellomo et al., Acute renal failure—definition, outcome measures, animal models, fluid therapy and information technology needs: the Second International Consensus Conference of the Acute Dialysis Quality Initiative (ADQI) Group. Crit Care. Aug. 2004;8(4):R204-212.
Bone et al., Definitions for sepsis and organ failure and guidelines for the use of innovative therapies in sepsis. The ACCP/SCCM Consensus Conference Committee. American College of Chest Physicians/Society of Critical Care Medicine. Chest. Jun. 1992;101(6):1644-1655.
Chertow et al., Acute kidney injury, mortality, length of stay, and costs in hospitalized patients. J Am Soc Nephrol. Nov. 2005;16(11):3365-3370.
Cwirla et al., Peptides on phage: a vast library of peptides for identifying ligands. Proc Natl Acad Sci U S A. Aug. 1990;87(16):6378-6382.
Devlin et al., Random Peptide Libraries: A Source of Specific Protein Binding Molecules. Science. Jul. 27, 1990;249(4967):404-406.
Fischer et al., A readers' guide to the interpretation of diagnostic test properties: clinical example of sepsis. Intensive Care Med. Jul. 2003;29(7):1043-1051.
Hanley and Mcneil, The Meaning and Use of the Area under a Receiver Operating Characteristic (ROC) Curve. Radiology. Apr. 1982;143(1):29-36.
Jaimes et al., The systemic inflammatory response syndrome (SIRS) to identify infected patients in the emergency room. Intensive Care Med. Aug. 2003;29(8):1368-1371.
Kellum, Acute kidney injury. Crit Care Med. Apr. 2008;36(4 Suppl):S141-S145.
Lassnigg et al., Minimal changes of serum creatinine predict prognosis in patients after cardiothoracic surgery: a prospective cohort study. J Am Soc Nephrol. Jun. 2004;15(6):1597-1605.
Llewelyn and Cohen, Diagnosis of infection in sepsis. Intensive Care Med. 2001;27 Suppl 1:S10-S32.
Mccullough et al., Contrast-Induced Nephropathy (CIN) Consensus Working Panel: executive summary. Rev Cardiovasc Med. 2006 Fall;7(4):177-197.
Mehta et al., Acute Kidney Injury Network: report of an initiative to improve outcomes in acute kidney injury. Crit Care. 2007;11(2):R31.
Nelson and Griswold, A computer program for calculating antibody affinity constants. Comput Methods Programs Biomed. Jul.-Aug. 1988;27(1):65-68.
Praught and Shlipak, Are small changes in serum creatinine an important risk factor? Curr Opin Nephrol Hypertens. May 2005;14(3):265-270.
Ricci et al., The RIFLE criteria and mortality in acute kidney injury: A systematic review. Kidney Int. Mar. 2008;73(5):538-546.
Ronco et al., POTENTIAL Interventions in Sepsis-Related Acute Kidney Injury. Clin J Am Soc Nephrol. Mar. 2008;3(2):531-544.
Scott and Smith, Searching for Peptide Ligands with an Epitope Library. Science. Jul. 27, 1990;249(4967):386-390.
Van Erp et al., Application of a sol particle immunoassay to the determination of affinity constants of monoclonal antibodies. J Immunoassay. 1991;12(3):425-443.
Ward et al., Binding activities of a repertoire of single immunoglobulin variable domains secreted from *Escherichia coli*. Nature. Oct. 12, 1989;341(6242):544-546.

(56) References Cited

OTHER PUBLICATIONS

Wilson et al., Simplified conjugation chemistry for coupling peptides to F(ab') fragments: autologous red cell agglutination assay for HIV-1 antibodies. J Immunol Methods. Oct. 14, 1994;175(2):267-273.

Yarmush et al., Coupling of antibody-binding fragments to solid-phase supports: site-directed binding of F(ab') 2 fragments. J Biochem Biophys Methods. Dec. 1992;25(4):285-297.

Zarjou and Agarwal, Sepsis and Acute Kidney Injury. J Am Soc Nephrol. Jun. 2011;22(6):999-1006.

Extended European Search Report issued in EP12854991 dated Oct. 2, 2015.

Etzioni et al., "Combining biomarkers to detect disease with application to prostate cancer", Biostatistics. Oct. 2003;4(4):523-38.

Honore et al., "Urinary Tissue Inhibitor of Metalloproteinase-2 and Insulin-Like Growth Factor-Binding Protein 7 for Risk Stratification of Acute Kidney Injury in Patients With Sepsis", Crit Care Med. Oct. 2016;44(10):1851-60. doi: 10.1097/CCM.0000000000001827.

Lu et al., "Biomarker detection in the integration of multiple multi-class genomic studies", Bioinformatics. Feb. 1, 2010;26(3):333-40. doi: 10.1093/bioinformatics/btp669. Epub Dec. 4, 2009.

Mamtani et al., "A simple method to combine multiple molecular biomarkers for dichotomous diagnostic classification", BMC Bioinformatics. Oct. 10, 2006;7:442.

Yuan et al., "Combining multiple biomarker models in logistic regression", Biometrics. Jun. 2008;64(2):431-9. doi: 10.1111/j.1541-0420.2007.00904.x. Epub Mar. 5, 2008.

KDIGO Clinical Practice Guideline for Acute Kidney Injury, Kidney International, 2 (Suppl 1): 1-141, Mar. 2012.

Abd El Latif et al., "Urinary Epidermal Growth Factor Excretion: A Useful Prognostic Marker for Progression of Renal Damage in Children," J Med Sci, Oct. 1, 2007, 7(7):1171-1176.

Abou-Shousha et al., "Interleukin-2 Regulatory Effect on P-Selectin and Interleukin-8 Production in Patients with Chronic Renal Failure," Egypt J Immunol, 2006, 13(1):11-18.

Akcay et al., "Mediators of Inflammation in Acute Kidney Injury," Mediators Inflamm, 2009, 2009:137072 (12 pp).

Albright, "Acute Renal Failure: A Practical Update," Mayo Clin Proc, Jan. 2001, 76(1):67-74.

Amemiya et al., "Insulin like growth factor binding protein-7 reduces growth of human breast cancer cells and xenografted tumors," Breast Cancer Res Treat, May 2010 (pub online), 126:373-384.

Anders et al., "Chemokines and chemokine receptors are involved in the resolution or progression of renal disease," Kidney Int, 2003, 63(2):401-415.

Anilkumar et al., "Trimeric assembly of the C-terminal region of Thrombospondin-1 or Thrombospondin-2 is necessary for cell spreading and fascin spike organization," J Cell Sci, 2002, 115(11):2357-2366.

Aregger et al., "Identification of IGFBP-7 by urinary proteomics as a novel prognostic marker in early acute kidney injury," Kidney International, 2014, 85(4):909-919.

Arribas et al., "ADAM17 as a Therapeutic Target in Multiple Diseases," Curr Pharm Des, 2009, 15(20):2319-2335.

Arrizabalaga et al., "Tubular and Interstitial Expression of ICAM-1 as a Marker of Renal Injury in IgA Nephropathy," Am J Nephrol, Jan. 2003, 23(3):121-128.

Bagshaw et al., "Urinary biomarkers in septic acute kidney injury," Intensive Care Med, May 2007, 33(7):1285-1296.

Bajwa et al., "Immune Mechanisms and Novel Pharmacological Therapies of Acute Kidney Injury," Curr Drug Targets, 2009, 10(12):1196-1204.

Barrera-Chimal et al., "Hsp72 is an early and sensitive biomarker to detect acute kidney injury," EMBO Mol Med, 2011, 3(1):5-20.

Basile et al., "Renal ischemia reperfusion inhibits VEGF expression and induces ADAMTS-1, a novel VEGF inhibitor," Am J Physiol Renal Physiol, Feb. 6, 2008, 294(4):F928-F936.

Bennett et al., "Chronic cyclosporine nephropathy: The Achilles' heel of immunosuppressive therapy," Kidney Int., 1996, 50(4):1089-1100.

Berahovich et al., "Proteolytic Activation of Alternative CCR1 Ligands in Inflammation," J Immunol, Jun. 2005, 174(11):7341-7351.

Beushausen, "NWG Biomarker Objectives," ILSI Health and Environmental Sciences Institute, ILSI-HESI Annual Meeting, 2006, 17 pp.

Bicik et al., "Role of Transforming Growth Factor-beta2 in, and a Possible Transforming Growth Factor-beta2 Gene Polymorphism as a Marker of, Renal Dysfunction in Essential Hypertension: A Study in Turkish Patients," Current Therapeutic Research, Jul./Aug. 2005, 66(4):266-278.

Bihorac et al., "Validation of Cell-Cycle Arrest Biomarkers for Acute Kidney Injury Using Clinical Adjudication," Am J Respir Crit Care Med., Feb. 2014 (originally published), 189(8):932-939.

Biotrin International, "Biotrin Biomarkers: How late do you want to detect preclinical kidney damage?," Biotrin's acute kidney injury test (AKI Test), Biotrin's Preclinical Kidney Biomarkers, 8 pp.

Bone et al., "Definitions for Sepsis and Organ Failure and Guidelines for the Use of Innovative Therapies in Sepsis," American College of Chest Physicians/Society of Critical Care Medicine, Jun. 1992, 101(6):1644-55.

Bonomini et al., "Serum Levels of Soluble Adhesion Molecules in Chronic Renal Failure and Dialysis Patients," Nephron, 1998, 79(4):399-407.

Bonventre, "Dedifferentiation and Proliferation of Surviving Epithelial Cells in Acute Renal Failure," J Am Soc Nephrol, 2003, 14(Suppl 1):S55-S61.

Bonventre, "Pathophysiology of Acute Kidney Injury: Roles of Potential Inhibitors of Inflammation," Contrib Nephrol, 2007, 156:39-46.

Bonventre et al., "Ischemic acute renal failure: An inflammatory disease?," Kidney Int, Aug. 2004, 66(2):480-485.

Burne et al., "IL-1 and TNF independent pathways mediate ICAM-1/VCAM-1 up-regulation in ischemia reperfusion injury," J Leukoc Biol, Aug. 2001, 70(2):192-198.

Burne-Taney et al., "The role of adhesion molecules and T cells in ischemic renal injury," Curr Opin Nephrol Hypertens, 2003, 12(1):85-90.

Cai, "Detection and Application for the biomarker of Renal Injury in Early Stage," Laboratory Med Clinic, 2005, 2(3):124-127—with English translation.

Calabrese et al., "Oxidative stress and cellular stress response in diabetic nephropathy," Cell Stress & Chaperones, 2007, 12(4):299-306—Accession No. XP002705326.

Canani et al., "The Fatty Acid-Binding Protein-2 A54T Polymorphism Is Associated With Renal Disease in Patients With Type 2 Diabetes," Diabetes, Nov. 2005, 54(11):3326-3330.

Catania et al., "Role of matrix metalloproteinases in renal pathophysiologies," Am J Physiol Renal Physiol, Dec. 2006 (first published), 292(3):F905-F911.

Chawla et al., "Identifying critically ill patients at high risk for developing acute renal failure: A pilot study," Kidney Int., 2005, 68(5):2274-2280.

Choi et al., "Expression of Vascular Endothelial Growth Factor-C and its Receptor mRNA in the Rat Kidney with Ischemia-Reperfusion Injury," Clinical Kidney J, Jun. 2, 2011, 4(S2):2 pp.

Christenson et al., "Standardization of Cardiac Troponin I Assays: Round Robin of Ten Candidate Reference Materials," Clinical Chemistry, 2001, 47(3):431-437.

Coca et al., "Biomarkers for the diagnosis and risk stratification of acute kidney injury: A systematic review," Kidney Int, Dec. 2007 (pub online), 73:1008-1016.

Cooper, "Effect of tobacco smoking on renal function," Indian J Med Res, Sep. 2006, 124(3):261-268.

Cottone et al., "Endothelin-1 and F2-isoprostane relate to and predict renal dysfunction in hypertensive patients," Nephrol Dial Transpl, Sep. 2008 (advance access pub), 24(2):497-503.

(56) References Cited

OTHER PUBLICATIONS

Cruz et al., North East Italian Prospective Hospital Renal Outcome Survey on Acute Kidney Injury (NEiPHROS-AKI): Targeting the Problem with the Rifle Criteria, Clin J Amer Soc Nephrol, Mar. 2007 (Epub), 2(3):418-425.
Cutillas et al., "The urinary proteome in Fanconi syndrome implies specificity in the reabsorption of proteins by renal proximal tubule cells," Am J Physiol Renal Physio, May 2004, 287(3):F353-F364.
Daemen et al., "Apoptosis and Chemokine Induction After Renal Ischemia-Reperfusion," Transplantation, Apr. 15, 2001, 71(7):1007-1011.
Daha et al., "Is the proximal tubular cell a proinflammatory cell?," Nephrol Dial Transplant, 2000, 15(Suppl 6):41-43.
De Sá et al., "Leukocyte, Platelet and Endothelial Activation in Patients with Acute Renal Failure Treated by Intermittent Hemodialysis," Am J Nephrol, 2001, 21(4):264-273.
Devarajan, "Cellular and molecular derangements in acute tubular necrosis," Curr Opin Pediatr, 2005, 17(2):193-199.
Devarajan, "Novel biomarkers for the early prediction of acute kidney injury," Cancer Therapy, Sep. 2005, 3:477-488.
Devarajan et al., "Proteomics for Biomarker Discovery in Acute Kidney Injury," Semin Nephrol, Nov. 2007, 27(6):637-651.
Devarajan, "Update on Mechanisms of Ischemic Acute Kidney Injury," J Am Soc Nephrol, 2006, 17:1503-1520.
Devlin et al., "Random Peptide Libraries: A Source of Specific Protein Binding Molecules," Science, Jul. 27, 1990, 249(A967):404-406.
Domanski et al., "Purine and Cytokine Concentrations in the Renal Vein of the Allograft During Reperfusion," Transplant Proc, 2007, 39(5):1319-1322.
Edelstein, "Biomarkers of Acute Kidney Injury," Adv Chronic Kidney Dis., Jul. 2008, 15(3)222-234.
El Sabbahy et al., "Ischemic kidney injury and mechanisms of tissue repair," Wiley Interdiscip Rev Syst Biol Med, Dec. 2010 (Epub), 3(5):606-618.
Endo et al., "Matrix metalloproteinase-2, matrix metalloproteinase-9, and tissue inhibitor of metalloproteinase-1 in the peripheral blood of patients with various glomerular diseases and their implication in pathogenetic lesions: study based on an enzyme-linked assay and immunohistochemical staining," Clin Exp Nephrol, Dec. 2006, 10(4):253-261.
FDA, "European Medicines Agency to Consider Additional Test Results When Assessing New Drug Safety—Collaborative effort by FDA and EMEA expected to yield additional safety data," Jun. 12, 2008, http://www.natap.org/2008/ newsUpdates/071608_01.htm.
FDA News Release, U.S. Food and Drug Administration, FDA allows marketing of the first test to assess risk of developing acute kidney injury, Sep. 5, 2014 https://www.fda.gov/NewsEvents/Newsroom/PressAnnouncements/ucm412910.htm.
Ferguson et al., "Biomarkers of nephrotoxic acute kidney injury," Toxicology, Jan. 2008, 245(3):182-193.
Flynn et al., "Urinary excretion of beta2-glycoprotein-1 (apolipoprotein H) and other markers of tubular malfunction in "non-tubular" renal disease," J Clin Pathol, 1992, 45(7):561-567.
Frangoiannis, "Chemokines in ischemia and reperfusion," Thromb Haemost, Apr. 2007, 97(5):738-747.
Fried et al., "Inflammatory and Prothrombotic Markers and the Progression of Renal Disease in Elderly Individuals," J Am Soc Nephrol, Dec. 2004, 15(12):3184-3191.
Fu et al., "Study on the expression of VEGF, MMP-2 and TIMP-2 in the progression of IgA nephropathy," J Clin Exp Pathol, Oct. 2008, 24(5):573-576—Abstract only.
Fujisaki et al., "Infusion of radiocontrast agents induces exaggerated release of urinary endothelin in patients with impaired renal function," Clin Exp Nephrol, Dec. 2003, 7(4):279-283.
Furuichi et al., "Chemokine/chemokine receptor-mediated inflammation regulates pathologic changes from acute kidney injury to chronic kidney disease," Clin Exp Nephrol, Dec. 2008 (Epub), 13(1):9-14.

Furuichi et al., "Roles of chemokines in renal ischemia/reperfusion injury," Front Biosci, May 1, 2008, 13:4021-4028.
Galkina et al., "Leukocyte Recruitment and Vascular Injury in Diabetic Nephropathy," J Am Soc Nephrol, Jan. 2006 (Epub), 17(2):368-377.
Garcia et al., "Adenosine A2A receptor activation and macrophage-mediated experimental glomerulonephritis," FASEB J, 2008, 22(2):445-454.
Gbadegesin et al., "Plasma and urinary soluble adhesion molecule expression is increased during first documented acute pyelonephritis," Arch Dis Child, 2002, 86(3):218-221.
Gocze et al., "Urinary Biomarkers TIMP-2 and IGFBP7 Early Predict Acute Kidney Injury after Major Surgery," PLoS ONE, Mar. 23, 2015, DOI:10.1371/journal.pone.0120863, pp. 1-11.
Goes et al., "Effect of Recombinant Human Insulin-Like Growth Factor-1 on the Inflammatory Response to Acute Renal Injury," J Am Soc Nephrol, 1996, 7(5):710-720.
Goldstein et al., "Renal Angina," Clin J Am Soc Nephrol, 2010, 5(5):943-949.
Grigoryev et al., "The Local and Systemic Inflammatory Transcriptome after Acute Kidney Injury," J Am Soc Nephrol, 2008, 19(3):547-558.
Gümüs et al., "Serum Levels of Total Acid Phosphatase, Prostatic Acid Phosphatase, Total and Free Prostate-Specific Antigen in Patients Within Chronic Hemodialysis Program," Braz J Urol, Mar.-Apr. 2001, 27(2):133-135.
Gupta et al., "Role of Protein C in Renal Dysfunction after Polymicrobial Sepsis," J Am Soc Nephrol., Mar. 18, 2007, (3):860-867.
Haase et al., "A comparison of the RIFLE and Acute Kidney Injury Network classifications for cardiac surgery-associated acute kidney injury: A prospective cohort study," J Thorac Cardiovasc Surg, Dec. 2009, 138(6):1370-1376.
Han, "Biomarkers for Early Detection of Acute Kidney Injury," Nephrology Rounds, Apr. 2008, 6(4):6 pp.
Han et al., "Upregulation of hyaluronan and its binding receptors in an experimental model of chronic cyclosporine nephropathy," Nephrology, 2010, 15(2):216-224.
Han et al., "Urinary biomarkers in the early diagnosis of acute kidney injury," Kidney Int, Dec. 2007 (pub online), 73(7):863-869.
Han et al., "Urinary Biomarkers in the Early Diagnosis of Acute Kidney Injury after Cardiac Surgery," Clin J Am Soc Nephrol, Apr. 2009 (Epub), 4(5):873-882.
Harpur et al., "Biological Qualification of Biomarkers of Chemical-Induced Renal Toxicity in Two Strains of Male Rat," Toxicol Sci., May 2011 (advance access pub), 122(2):235-252.
Harris et al., "Growth Factors and Cytokines in Acute Renal Failure," Adv Ren Replace Ther, Apr. 1997, 4(2 Suppl):43-53.
Hatta et al., "Cytokine Array Comparisons of Plasma from Cycling Fertile Women on Cycle Day 5 and Ovulation," Am J Reprod Immunol, Sep. 2009, 62(3):158-164.
He et al., "A research on serum, urine and tumor tissue hyaluronate assays for detecting malignant ovarian tumors," Zhonghua Fu Chan Ke Za Zhi, Mar. 1995, 30(3):161-163 (abstract only ).
He et al., "Interleukin-18 binding protein transgenic mice are protected against ischemic acute kidney injury," Am J Physiol Renal Physiol, Aug. 2008, 295(5):F1414-F1421.
Healy et al., "Apoptosis and necrosis: Mechanisms of cell death induced by cyclosporine A in a renal proximal tubular cell line," Kidney Int, 1998, 54(6):1955-1966.
Herget-Rosenthal et al., "Early detection of acute renal failure by serum cystatin C," Kidney Int, 2004, 66(3):1115-1122.
Hidaka et al., "Urinary clusterin levels in the rat correlate with the severity of tubular damage and may help to differentiate between glomerular and tubular injuries," Cell Tissue Res, Oct. 2002, 310(3):289-296.
Hirai et al., "Plasma Endothelin-1(ET-1) is a Useful Marker for Renal Dysfunction," Atheroscler Suppl., Jun. 19, 2006, 7(3):60[Mo-P1:65].
Hirschberg et al., "Factors Predicting Poor Outcome in Patients with Acute Renal Failure (ARF)," J Am Soc Nephrol, Sep. 1, 1996, 7(9):1374.

(56) References Cited

OTHER PUBLICATIONS

Hoste et al., "RIFLE criteria for acute kidney injury are associated with hospital mortality in critically ill patients: a cohort analysis.," Crit Care, May 2006, 10(3):R73, 10 pp.

Hugo et al., "Thrombospondin 1 precedes and predicts the development of tubulointerstitial fibrosis in glomerular disease in the rat," Kidney Int, 1998, 53(2):302-311.

Hugo et al., "Thrombospondin in Renal Disease," Nephron Exp Nephrol, Jan. 2009, 111(3):e61-e66.

Humphreys et al., "Mesenchymal Stem Cells in Acute Kidney Injury," Annu Rev Med, 2008, 59:311-325.

Iglesias et al., "Thyroid Dysfunction and Kidney Disease (Revised version)," Eur J Endocrinol, Dec. 18, 2008, pp. 1-32 retrieved from URL://www.eje.org/content!early/2008/12/18/EJE-08-0837.full.pdf.

Jang et al., "The innate immune response in ischemic acute kidney injury," Clin Immunol, Oct. 2008 (Epub), 130(1):41-50.

Jonsson, "The role of fibroblast growth factor 23 in renal disease," Nephrol Dial Transplant, Mar. 2005, 20(3):479-482.

Julian et al., "Sources of Urinary Proteins and their Analysis by Urinary Proteomics for the Detection of Biomarkers of Disease," Proteomics Clin Appl., Aug. 26, 2009, 3(9):1029-1043.

Jung et al., "Diagnostic Significance of Urinary Enzymes in Detecting Acute Rejection Crises in Renal Transplant Recipients Depending on Expression of Results Illustrated Through the Example of Alanine Aminopeptidase," Clin Biochem, Aug. 1985, 18(4):257-260.

Kadiroglu et al., "The Evaluation of Effects of Demographic Features, Biochemical Parameters, and Cytokines on Clinical Outcomes in Patients with Acute Renal Failure," Renal Failure, 2007, 29(4):503-508.

Kalousová et al., "Soluble Receptor for Advanced Glycation End Products in Patients With Decreased Renal Function," Am J Kidney Dis, Mar. 2006, 47(3):406-411.

Kamata et al., "Up-regulation of glomerular extracellular matrix and transforming growth factor-beta expression in RF/J mice," Kidney Int, 1999, 55(3):864-876.

Kamimoto et al., "Hepatocyte growth factor prevents multiple organ injuries in endotoxemic mice through a heme oxygenase-1-dependent mechanism," Biochem Biophys Res Commun, Jan. 2009 (Epub), 380(2):333-337.

Kasahara et al., "Clinical Significance of Serum Oxidized Low-Density Lipoprotein/beta2-Giycoprotein I Complexes in Patients with Chronic Renal Diseases," Nephron Clin Pract, 2004, 98(1):c15-c24.

Kashani et al., "Discovery and validation of cell cycle arrest biomarkers in human acute kidney injury," Critical Care, Feb. 2013, 17(R25):1-12.

Keightley, "A comparison of manual and robotic pipetting for plate-based assays," Laboratory Practice, 1989, 38(10):53-55.

Kehoe et al., "Elevated Plasma Renin Activity Associated with Renal Dysfunction," Nephron, 1986, 44(1):51-57 (abstract only).

Kellum et al., "Definition and Classification of Acute Kidney Injury," Nephron Clin Pract, Sep. 2008, 109(4):c182-c187.

Keyes et al., "Early diagnosis of acute kidney injury in critically ill patients," Expert Rev Mol Diagn, Jul. 2008, 8(4):455-464.

Khanna et al., "Expression of TGF-beta and fibrogenic genes in transplant recipients with tacrolimus and cyclosporine nephrotoxicity," Kidney Int, 2002, 62(6):2257-2263.

Kharasch et al., "Gene Expression Profiling of Nephrotoxicity from the Sevoflurane Degradation Product Fluoromethyl-2,2-difluoro-1-(trifluoromethyl)vinyl Ether ("Compound A") in Rats," Toxicol Sci, Oct. 2005 (advance access pub), 90(2):419-431.

Kierdorf et al., "Continuous Renal Replacement Therapies Versus Intermittent Hemodialysis in Acute Renal Failure: What Do We Know?," American Journal of Kidney Diseases, Nov. 1996, 28(5)(Suppl 3):S90-S96.

Kiley et al., "Urinary biomarkers: the future looks promising," Kidney Int, Jul. 2009, 76(2):133-134.

Kilis-Pstrusinska et al., [Levels of selected soluble adhesion molecules in blood serum of children with chronic glomerulonephritis]. Pol Merkur Lekarski. Apr. 2001;10(58):247-249—English transl abstract only.

Kilis-Pstrusinska et al., "Serum Levels of Soluble Adhesion Molecules in Children with Glomerulonephritis (GN)," Nephrol Dialysis Transplant, Jun. 2001, 16(6):A62.

Kimmel et al., "Immunologic function and survival in hemodialysis patients," Kidney Int, Jul. 1998, 54(1):236-244.

Kingsmore et al., "Multiplexed protein profiling on antibody-based microarrays by rolling circle amplification," Current Opin Biotechnol, Feb. 2003, 14:74-81.

Kinsey et al., "Inflammation in Acute Kidney Injury," Nephron Exp Nephrol, Sep. 2008 (Epub), 109(4):e102-e107.

Koo et al., "Cadaver versus living donor kidneys: Impact of donor factors on antigen induction before transplantation," Kidney Int., Oct. 1999, 56(4):1551-1559.

Kos et al., "Cathepsins B, H, and L and Their Inhibitors Stefin A and Cystatin C in Sera of Melanoma Patients," Clin Cancer Res, Oct. 1997, 3(10):1815-1822.

Kunugi et al., "Inhibition of matrix metalloproteinases reduces ischemia-repertusion acute kidney injury," Lab Invest, Oct. 2010 (Epub), 91(2):170-180.

Kutsukake et al., "Circulating IGF-binding protein 7 (IGFBP7) levels are elevated in patients with endometriosis or undergoing diabetic hemodialysis," Reproductive Biology and Endocrinology, Nov. 2008, 6:54, 6 pp.

Lan, "Clinical significance of determination of serum hyaluronic acid, type III procollagen, collagen IV and laminin in patients with nephropathy," J Guangxi Med Univ, Oct. 2002, 19(5):655-656—English translation of abstract only.

Landray et al., "Inflammation, Endothelial Dysfunction, and Platelet Activation in Patients With Chronic Kidney Disease: The Chronic Renal Impairment in Birmingham (CRIB) Study," Am J Kidney Dis, Feb. 2004, 43(2):244-253.

Lang et al., "Heat Shock Protein 60 Is Released in Immune-Mediated Glomerulonephritis and Aggravates Disease: In Vivo Evidence for an Immunologic Danger Signal," J Am Soc Nephrol, Dec. 2004 (Epub), 16(2):383-391.

Lapsley et al., "Beta2-glycoprotein-1 (apolipoprotein H) excretion in chronic renal tubular disorders: Comparison with other protein markers of tubular malfunction," J Clin Pathol, 1991, 44(10):812-816.

Larsson et al., "Circulating concentration of FGF-23 increases as renal function declines in patients with chronic kidney disease, but does not change in response to variation in phosphate intake in healthy volunteers," Kidney Int, Dec. 2003, 64(6):2272-2279.

Lemay et al., "Prominent and Sustained Up-Regulation of GP130-Signaling Cytokines and of the Chemokine MIP-2 in Murine Renal Ischemia-Reperfusion Injury," Transplantation, Mar. 15, 2000, 69(5):959-63.

Li et al., Predictive value of RIFLE classification on prognosis of critically ill patients with acute kidney injury treated with continuous renal replacement therapy, Chin Med J (Engl), May 5, 2009, 122(9):1020-1025.

Liu et al., "Predictive and pathogenetic value of plasma biomarkers for acute kidney injury in patients with acute lung injury," Crit Care Med, Dec. 2007, 35(12):2755-2761.

Liu et al., "Serum Interleukin-6 and interleukin-8 are early biomarkers of acute kidney injury and predict prolonged mechanical ventilation in children undergoing cardiac surgery: a case-control study," Critical Care, Jul. 2009 (Epub), 13(4):R104 (9 pp).

Lopes-Virella et al., "Urinary High Density Lipoprotein in Minimal Change Glomerular Disease and Chronic Glomerulopathies," Clin Chim Acta, 1979, 94(1):73-81.

Lu et al., "Increased Macrophage Infiltration and Fractalkine Expression in Cisplatin-Induced Acute Renal Failure in Mice," J Pharmacol Exp Ther, Oct. 2007 (Epub), 324(1):111-117.

Maccallum et al., "Antibody-antigen Interactions: Contact Analysis and Binding Site Topography," J Mol Biol, 1996, 262:732-745.

Maddens et al., "Chitinase-like Proteins are Candidate Biomarkers for Sepsis-induced Acute Kidney Injury," Mol Cell Proteomics, Jan. 10, 2012, 11(6):1-13.

(56) References Cited

OTHER PUBLICATIONS

Maier et al., "Massive Chemokine Transcription in Acute Renal Failure Due to Polymicrobial Sepsis," Shock, Aug. 2000, 14(2):187-192.
Malm et al., "Changes in the plasma levels of vitamin K-dependent proteins C and S and of C4b-binding protein during pregnancy and oral contraception," Br J Haematol, Apr. 1988, 68(4):437-443.
Malyszko et al., "Visfatin and apelin, new adipocytokines, and their relation to endothelial function in patients with chronic renal failure," Adv Med Sci, 2008, 53(1):32-36.
Mamtani et al., "A simple method to combine multiple molecular biomarkers for dichotomous diagnostic classification," BMC Bioinformatics, Oct. 10, 2006, 7:442, 12 pp.
Mast et al., "Clinical utility of the soluble transferrin receptor and comparison with serum ferritin in several populations," Clin Chem, Jan. 1998, 44(1):45-51.
Matousovic et al., "IgA-containing immune complexes in the urine of IgA nephropathy patients," Nephrol Dial Transplant, Jun. 2006 (Epub), 21:2478-2484.
Matsuda et al., "Beta2-Glycoprotein I-Dependent and -Independent Anticardiolipin Antibody in Patients with End-Stage Renal Disease," Thromb Res., Oct. 15, 1993, 72(2):109-117.
Matsuzaka et al., "Relationship between vitamin K dependent coagulation factors and anticoagulants (protein C and protein S) in neonatal vitamin K deficiency," Arch Dis Childhood, Mar. 1993, 68:297-302.
Mattes, "Experience With a Biomarker Consortium," CPath Predictive Safety Training Consortium, Critical Path Institute, 48 pp.
Mazanowska et al., "Imbalance of Metallaproteinase/Tissue Inhibitors of Metalloproteinase System in Renal Transplant Recipients With Chronic Allograft Injury," Transplant Proc, Oct. 2011, 43(8):3000-3003.
Meersch et al., "Urinary TIMP-2 and IGFBP7 as Early Biomarkers of Acute Kidney Injury and Renal Recovery following Cardiac Surgery," PLoS One, Mar. 2014; 9(3):e93460, 9 pp.
Meersch et al., "Validation of Cell-Cycle Arrest Biomarkers for Acute Kidney Injury after Pediatric Cardiac Surgery," PLoS One, Oct. 2014, 9(10):e110865 (6 pp).
Mehran et al., "A Simple Risk Score for Prediction of Contrast-Induced Nephropathy After Percutaneous Coronary Intervention: Development and Initial Validation," J Am Coll Cardiol, Oct. 2004, 44(7):1393-1399.
Melnikov et al., "Impaired IL-18 processing protects caspase-1-deficient mice from ischemic acute renal failure," J Clin Invest, May 2001, 107(9):1145-1152.
Mezzano et al., "Endothelial Cell Markers in Chronic Uremia: Relationship with Hemostatic Defects and Severity of Renal Failure," Thromb Res, Dec. 15, 1997, 88(6):465-472.
Milford et al., "Prognostic Markers in Diarrhoea-Associated Haemolytic-Uraemic Syndrome: Initial Neutrophil Count, Human Neutrophil Elastase and Von Willebrand Factor Antigen," Nephrol Dial Transplant, 1991, 6(4):232-237.
Mishra et al., "Neutrophil gelatinase-associated lipocalin (NGAL) as a biomarker for acute renal injury after cardiac surgery," Lancet, Apr. 2005, 365(9466):1231-1238.
Miura et al., "Neutralization of Gro(alpha) and Macrophage Inflammatory Protein-2 Attenuates Renal Ischemia/Reperfusion Injury," Am J Pathol., Dec. 2001, 159(6):2137-2145.
Molls et al., "Keratinocyte-derived chemokine is an early biomarker of ischemic acute kidney injury," Am J Physiol Renal Physiol, Dec. 2005 (Epub), 290(5):F1187-F1193.
Montagna et al., "Impairment of cellular redox status and membrane protein activities in kidneys from rats with ischemic acute renal failure," Biochim Biophys Acta, Aug. 1998, 1407(2):99-108.
Musial et al., "The Heat Shock Protein Profile in Children with Chronic Kidney Disease," Pent Dial Int., Jan. 2010 (Epub), 30(2):227-232.
Musial et al., "Soluble Adhesion Molecules in Chronic Renal Failure (CRF) Children Treated Conservatively," Nephrol Dialysis Transplant, 2002, 17(Abstracts Suppl 1):232.

Nambi et al., "Down regulation of kidney neutral endopeptidase mRNA, protein and activity during acute renal failure: Possible mechanism for ischemia-induced acute renal failure in rats?," Mol Cell Biochem, Jul. 1999, 197(1-2):53-59.
Nelson et al., "A computer program for calculating antibody affinity constants," Comput Methods Programs Biomed, Jul.-Aug. 1988, 27(1):65-68.
Neziri et al., "Cloning and molecular characterization of Dashurin encoded by C20orf116, a PCI-domain containing protein," Biochim Biophys Acta, Dec. 2009 (Epub), 1800(4):430-438.
Nguyen et al., "Biomarkers for the early detection of acute kidney injury," Pediatr Nephrol, Mar. 2007 (Epub), 23:2151-2157.
Nguyen et al., "Heparin-Binding EGF-Like Growth Factor Is Up-Regulated in the Obstructed Kidney in a Cell- and Region-Specific Manner and Acts to Inhibit Apoptosis," Am J Pathol, Mar. 2000, 156(3):889-898.
Nishiyama et al., "Up-Regulation of Galectin-3 in Acute Renal Failure of the Rat," Am J Pathol, Sep. 2000, 157(3):815-823.
Norman et al., "Progressive Renal Disease: Fibroblasts, Extracellular Matrix, and Integrins," Exp Nephrol, Mar.-Apr. 1999, 7(2):167-177.
Oh, "The insulin-like growth factor system in chronic kidney disease: Pathophysiology and therapeutic opportunities," Kidney Res Clin Pract, Jan. 2012 (Epub);31:26-37.
Ohno et al., "Prognostic significance of tenascin-C expression in clear cell renal cell carcinoma," Oncol Rep, Sep. 2008, 20(3):511-516.
Ozer et al., "A panel of urinary biomarkers to monitor reversibility of renal injury and a serum marker with improved potential to assess renal function," Nat Biotechnol, May 2010, 28(5):486-494.
Pajenda et al., "NephroCheck data compared to serum creatinine in various clinical settings," BMC Nephrology, Dec. 2015, 16:206, 7 pp.
Parikh et al., "New biomarkers of acute kidney injury," Crit Care Med, Apr. 2008, 36(4 Suppl):S159-S165.
Parikh et al., "Urinary IL-18 is an early predictive biomarker of acute kidney injury after cardiac surgery," Kidney Int, May 2006 (Epub), 70(1):199-203.
Paul, "Fundamental Immunology," Third Edition, Structure and Function of Immunoglobulins, 1993, 8:292-295.
Perco et al., "Protein biomarkers associated with acute renal failure and chronic kidney disease," Eur J Clin Invest, Nov. 2006, 36(11):753-763.
Picard et al., "Origin of renal myofibroblasts in the model of unilateral ureter obstruction in the rat," Histochem Cell Biol, May 2008 (Epub), 130(1):141-155.
Price, "Abrupt Changes in Prostate-Specific Antigen Concentration in Acute Renal Failure," Clin Chem, Jan. 1993, 39(1):161-162.
Prozialeck et al., "Cell Adhesion Molecules in Chemically-Induced Renal Injury," Pharmacol Ther, Jan. 2007 (Epub), 114(1):74-93.
Radford, Jr., et al., "Predicting Renal Outcome in IgA Nephropathy," J Am Soc Nephrol, Feb. 1997, 8(2):199-207.
Rajashekar et al., "Systemic diseases with renal manifestations," Prim Care, Jun. 2008, 35(2):297-328.abstract retrieved from URL:www.ncbi.nlm.nih.gov/pubmed/18486717.
Ramesh et al., "Endotoxin and cisplatin synergistically induce renal dysfunction and cytokine production in mice," Am J Physiol Renal Physiol, May 2007 (Epub), 293(1):F325-F332.
Ramesh et al., "TNF-α mediates chemokine and cytokine expression and renal injury in cisplatin nephrotoxicity," J Clin Invest, Sep. 2002, 110(6):835-842.
Ramirez et al., "Prospective Study on Autoantibodies Against Apolipoprotein H (Beta2GPI) in Several Clinical Parameters From Patients With Terminal Renal Failure and Functioning Renal Transplants," Transplantation Proceedings, Jul.-Aug. 2009, 41(6):2370-2372.
Ricci et al., "The RIFLE criteria and mortality in acute kidney injury: A systematic review," Kidney Int, Dec. 2007 (Epub), 73(5):538-546.
Ridker, "C-Reactive Protein: A Simple Test to Help Predict Risk of Heart Attack and Stroke," Circulation, Sep. 2003, 108:e81-e85, doi:10.1161/01.CIR.0000093381.57779.67.

(56) References Cited

OTHER PUBLICATIONS

Rini et al., "Renal cell carcinoma," Lancet, Mar. 2009;373(9669):1119-1132.
Ronco et al., "The concept of risk and the value of novel markers of acute kidney injury," Critical Care, Feb. 2013, 17(117):1-2.
Rosenkranz et al., "P-selectin deficiency exacerbates experimental glomerulonephritis: a protective role for endothelial P-selectin in inflammation," J Clin Invest, Mar. 1999, 103(5):649-659.
Rouschop et al., "Pre-transplant plasma and cellular levels of CD44 correlate with acute renal allograft rejection," Nephrol Dial Transplant, Oct. 2005, 20(10):2248-2254.
Rouschop et al., "Renal expression of CD44 correlates with acute renal allograft rejection," Kidney Int, Jul. 2006 (Epub), 70(6):1127-1134.
Sato et al., "Midkine Is Involved in Neutrophil Infiltration into the Tubulointerstitium in Ischemic Renal Injury," J Immunol, Sep. 15, 2001, 167(6):3463-3469.
Schaefer et al., "Urinary excretion of cathepsin B and cystatins as parameters of tubular damage," Kidney Int Suppl, Nov. 1994, 47:S64-S67.
Schaefer et al., "Insulin-like Growth Factor-I and the Kidney. Insulin-like Growth Factors," Kluwer Academic/Plenum Publishers, New York, 2003:244-261.
Schena et al., "EGF and MCP-1 Urinary Excretion Is a Suitable Prognostic Marker in IgA Nephropathy," J Am Soc of Nephrology, Meeting of the American Society of Nephrology, Sep. 1, 2002, 13(Program and Abstracts Issue): 458A.
Schiffer et al., "Activated Renal Macrophages Are Markers of Disease Onset and Disease Remission in Lupus Nephritis," J Immunol, Feb. 2008, 180(3):1938-1947.
Schmaldienst et al., "Angiogenin: A Novel Inhibitor of Neutrophil Lactoferrin Release during Extracorporeal Circulation," Kidney Blood Press Res, 2003, 26(2):107-112.
Schmidt et al., "Sexual hormone abnormalities in male patients with renal failure," Nephrol Dial Transplant, Mar. 2002, 17(3):368-371.
Schulz et al., "Endothelin-1 as an Early Prognostic Marker in Acute Renal Failure (ARF) and Sepsis," Kidney Blood Press Res, 2000, 23(3-5):341-342.
Segawa et al., "In situ expression and soluble form of P-selectin in human glomerulonephritis," Kidney Int, Oct. 1997, 52(4):1054-1063.
Segerer et al., "Chemokines, Chemokine Receptors, and Renal Disease: From Basic Science to Pathophysiologic and Therapeutic Studies," J Am Soc Nephrol, Jan. 2000, 11(1):152-176.
Senatorski et al., "Urine activity of cathepsin B, collagenase and urine excretion of TGF-beta1 and fibronectin in membranous glomerulonephritis," Res Exp Med (Berl), Dec. 1998, 198(4):199-206.
Severini et al., "Diagnostic significance of urinary enzymes: development of a high performance liquid chromatographic method for the measurement of urinary lysozyme," Clinica Chimica Acta, Feb. 1987, 163(1):97-103.
Sharma et al., "Two-dimensional fluorescence difference gel electrophoresis analysis of the urine proteome in human diabetic nephropathy," Proteomics, Jul. 2005, 5(10):2648-2655.
Shimoda et al., "Cathepsin G Is Required for Sustained Inflammation and Tissue Injury after Reperfusion of Ischemic Kidneys," Am J Pathol, Mar. 2007, 170(3):930-940.
Shlipak et al., "Elevations of Inflammatory and Procoagulant Biomarkers in Elderly Persons With Renal Insufficiency," Circulation, Jan. 2003, 107(1):87-92.
Shoji et al., "Plasma angiopoietin-like protein 3 (ANGPTL3) concentration is associated with uremic dyslipidemia," Atherosclerosis, May 2009 (Epub), 207(2):579-584.
Simmons et al., "Plasma cytokine levels predict mortality in patients with acute renal failure," Kidney Int, Apr. 2004, 65(4):1357-1365.
Song et al., "Expression of TRAIL, DR4, and DR5 in Kidney and Serum From Patients Receiving Renal Transplantation," Transplant Proc, Jun. 2004, 36(5):1340-1343.
Stafford-Smith et al., "Acute Kidney Injury and Chronic Kidney Disease After Cardiac Surgery," Adv Chronic Kidney Dis, Jul. 2008, 15(3):257-277.
Staško et al., "Soluble P-Selectin During a Single Hemodialysis Session in Patients With Chronic Renal Failure and Erythropoietin Treatment," Clin Appl Thromb Hemost, Oct. 2007, 13(4):410-415.
Stenvinkel et al., "High Serum Hyaluronan Indicates Poor Survival in Renal Replacement Therapy," Am J Kidney Dis, Dec. 1999, 34(6):1083-1088.
Stuard et al., "Soluble Adhesion Molecules in Chronic Renal Failure Patients," Nephrol Dialysis Transplant, 1997, 12(9):A100.
Sun et al., "Enhanced Expression of ANGPTL2 in the Microvascular Lesions of Diabetic Glomerulopathy," Nephron Exp Nephrol, Mar. 2007, 105(4):e117-e123.
Sun et al., "A Survey on the Relationship between the Epidermal Growth Factor and Renal Function," Int J Transpl Hemopurific, 2006, 4(1):41-44—English translation abstract only.
Supavekin et al., "Differential gene expression following early renal ischemia/repertusion," Kidney Int, May 2003, 63(5):1714-1724.
Sutton, "Alteration of microvascular permeability in acute kidney injury," Microvasc Res, Sep. 2008 (Epub), 77(1):4-7.
Sutton et al., "Injury of the renal microvascular endothelium alters barrier function after ischemia," Am J Physiol Renal Physiol, Apr. 2003 (Epub), 285(2):F191-F198.
Sutton et al., "Microvascular endothelial injury and dysfunction during ischemic acute renal failure," Kidney Int, Nov. 2002, 62(5):1539-1549.
Symon et al., "The endogenous insulin-like growth factor system in radiocontrast nephropathy," Am J Physiol, Mar. 1998, 274(3 Pt 2):F490-F497.
Takada et al., "The Cytokine-adhesion Molecule Cascade in Ischemia/Reperfusion Injury of the Rat Kidney, Inhibition by a Soluble P-selectin Ligand," J Clin Invest, Jun. 1997, 99(11):2682-2690.
Tan et al., "The level of urinary secretory immunoglobulin A (sIgA) of patients with IgA nephropathy is elevated and associated with pathological phenotypes," Clin Exp Immunol, Jan. 2009 (Epub), 156:111-116.
Tao et al., "Expression of 60-kDa and Inducible 70-kDa Stress Proteins in Gentamicin-Induced Acute Renal Failure," Clin Exp Nephrol, Jul. 1997, 1:254-260.
Tary-Lehmann et al., "Enzyme-Linked Immunosorbent Assay Spot Detection of Interferon-Gamma and Interleukin 5-Producing Cells as a Predictive Marker for Renal Allograft Failure," Transplantation, Jul. 27, 1998, 66(2):219-224.
Taulan et al., "Comprehensive analysis of the renal transcriptional response to acute uranyl nitrate exposure," BMC Genomics, Jan. 11, 2006, 7(2):1-14.
Teppo et al., "Soluble Intercellular Adhesion Molecule-1 (sICAM-1) after Kidney Transplantation: The Origin and Role of Urinary sICAM-1?," Transplantation, Apr. 27, 2001, 71(8):1113-1119.
Thakar et al., "A Clinical Score to Predict Acute Renal Failure after Cardiac Surgery," J Am Soc Nephrol, Nov. 2004 (Epub), 16:162-168.
Thakar et al., "Identification of thrombospondin 1 (TSP-1) as a novel mediator of cell injury in kidney ischemia," J Clin Invest, Nov. 2005 (Epub), 115(12):3451-3458.
Thiele et al., "AKI Associated with Cardiac Surgery," Clin J Ann Soc Nephrol, Nov. 2014 (Epub), 10:500-514.
Thorburn et al., "CXC and CC chemokines induced in human renal epithelial cells by inflammatory cytokines," APMIS, Jul. 2009, 117(7):477-487.
Thurman et al., "C3a Is Required for the Production of CXC Chemokines by Tubular Epithelial Cells after Renal Ishemia/Repertusion," J Immunol, Feb. 2007, 178:1819-1828.
Timoshanko et al., "Interleukin-12 from Intrinsic Cells Is an Effector of Renal Injury in Crescentic Glomerulonephritis," J Am Soc Nephrol, Mar. 2001, 12(3):464-471.
Torres et al., "The ratio of epidermal growth factor to monocyte chemotactic peptide-1 in the urine predicts renal prognosis in IgA nephropathy," Kidney Int, Oct. 2007 (Epub), 73(3):327-333.
Triage BNP Test Product Insert: Rapid Quantitative Test B-type Natriuretic Peptide, Alere Catalog #98000XR, 2011, 28 pp.

(56) References Cited

OTHER PUBLICATIONS

Vaidya et al., "Biomarkers of Acute Kidney Injury," Annu Rev Pharmacol Toxicol, 2008, 48:463-493.
Vaidya et al., "Mechanistic biomarkers for cytotoxic acute kidney injury," Expert Opin Drug Metab Toxicol, Oct. 2006, 2(5):697-713.
Vajdos et al., "Comprehensive Functional Maps of the Antigen-binding Site of an Anti-ErbB2 Antibody Obtained with Shotgun Scanning Mutagenesis," J Mol Biol, 2002, 320:415-428.
Vanhoutte et al., "Biomarker discovery with SELDI-TOF MS in human urine associated with early renal injury: evaluation with computational analytical tools," Nephrol Dial Transplant, Jul. 2007 (Epub), 22(10):2932-2943.
Villanueva et al., "Ischemic acute renal failure induces the expression of a wide range of nephrogenic proteins," Am J Physiol Regul Integr Comp Physiol, Nov. 2005 (Epub), 290(4):R861-R870.
Vonderscher, "Biomarker of Drug Induced Kidney Injury Qualification for Regulatory Decision Making," (CRADA). IOM/FDA, Silver Spring, MD, Apr. 2007, 23:1-31.
Voshol et al., "Evaluation of Biomarker Discovery Approaches to Detect Protein Biomarkers of Acute Renal Allograft Rejection," J Proteome Res, Jul.-Aug. 2005, 4(4):1192-1199.
Waikar et al., "Diagnosis, Epidemiology and Outcomes of Acute Kidney Injury," Clin J Am Soc Nephrol, Mar. 2008 (Epub), 3:844-861.
Waikar et al., "Imperfect Gold Standards for Kidney Injury Biomarker Evaluation," J Am Soc Nephrol, Oct. 2011 (Epub), 23(1):13-21.
Wan et al., "The pathogenesis of septic acute renal failure," Curr Opin Crit Care, Dec. 2003, 9:496-502.
Wang et al., "Netrin-1 and kidney injury. I. Netrin-1 protects against ischemia-reperfusion injury of the kidney," Am J Physiol Renal Physiol, Jan. 2008 (Epub), 294(4):F739-F747.
Wang et al., "Validation of putative genomic biomarkers of nephrotoxicity in rats," Toxicology, Jan. 2008 (Epub), 246:91-100.
Wen et al., "One dose of cyclosporine A is protective at initiation of folic acid-induced acute kidney injury in mice," Nephrol Dial Transplant, Jan. 2012 (Epub), 27:3100-3109.
Wetz et al., "Quantification of urinary TIMP-2 and IGFBP-7: an adequate diagnostic test to predict acute kidney injury after cardiac surgery?," Critical Care, Jan. 2015, 19:3, 7 pp.
Wijeysundera et al., "Derivation and Validation of a Simplified Predictive Index for Renal Replacement Therapy After Cardiac Surgery," JAMA, Apr. 25, 2007, 297:1801-1809.
Wilson et al., "Urinary Lysozyme: III. Lysozymuria in Children with the Nephrotic Syndrome," J Pediatr, Feb. 1950, 36(2):199-211.
Winchester et al., "Sorbents in Acute Renal Failure and End-Stage Renal Disease: Middle Molecule and Cytokine Removal," Blood Purif, 2004, 22(1):73-77.
Witzgall et al., "Localization of Proliferating Cell Nuclear Antigen, Vimentin, c-Fos, and Clusterin in the Postischemic Kidney: Evidence for a Heterogenous Genetic Response among Nephron Segments, and a Large Pool of Mitotically Active and Dedifferentiated Cells," J Clin Invest, May 1994, 93:2175-2188.
Yan et al., "Expression of MMP-2 and TIMP-1 in Renal Tissue of Patients with Chronic Active Antibody-Mediated Renal Graft Rejection," Diagn Pathol, Oct. 2012, 7:141, 6 pp.
Yang et al., "Acute renal failure during sepsis: Potential role of cell cycle regulation," J Infect, Apr. 2009 (Epub), 58:459-464.
Yang et al., "Frequency of anti-bactericidal/permeability-increasing protein (BPI) and anti-azurocidin in patients with renal disease," Clin Exp Immunol, Jul. 1996, 105(1):125-131.
Yang et al., "Remote Ischemic Preconditioning for Prevention of Acute Kidney Injury: A Meta-analysis of Randomized Controlled Trials," Am J Kidney Dis, Jun. 2014 (Epub), 64(4):574-583.
Yasuda et al., "Insulin like growth factor-1 increases p21 expression and attenuates cisplatin-induced acute renal injury in rats," Clin Exp Nephrol, Mar. 2004, 8:27-35.
Yasuda et al., "Simvastatin improves sepsis-induced mortality and acute kidney injury via renal vascular effects," Kidney Int, May 2006, 69(9):1535-1542.
Yu et al., "Urinary biomarkers trefoil factor 3 and albumin enable early detection of kidney tubular injury," Nat Biotechnol, May 2010, 128(5):470-477.
Yuen et al., "Ischemic and Nephrotoxic Acute Renal Failure are Distinguished by their Broad Transcriptomic Responses," Physiol Genomics, Feb. 2006 (Epub), 25(3):375-386.
Zaffanello et al., "Early diagnosis of acute kidney injury with urinary biomarkers in the newborn," J Matern-Fetal Neonatal Med, Oct. 2009, 22(Suppl 3):62-66.
Zager et al., "Proximal tubular cytochrome c efflux: Determinant, and potential marker, of mitochondrial injury," Kidney Int, Jun. 2004, 65(6):2123-2134.
Zhang et al., "The level of serum secretory IgA of patients with IgA nephropathy is elevated and associated with pathological phenotypes," Nephrol Dial Transplant, Oct. 2007 (Epub), 23:207-212.
Zheng et al., "Antiphospholipid antibody profiles in lupus nephritis with glomerular microthrombosis: a prospective study of 124 cases," Arthritis Research & Therapy, Jun. 2009, 11(R93):1-9.
Zhu et al., "Expression of Urinary Epidermal Growth Factor and Renal Function," J Clin Urol, 1998, 13(8):374-379 (abstract English translation).
Extended European Search Report dated Jul. 25, 2019, issued in European Application (No. 19151748.1).
Wiki: "Chronic kidney disease", Jan. 3, 2020, Retrieved from the internet: URL:https://en.wikipedia.org/wiki/Chronic_kidney_disease [retrieved on Jan. 7, 2020].

* cited by examiner

SEQUENCE LISTING

<160> NUMBER OF SEQ ID NOS: 24

<210> SEQ ID NO 1
<211> LENGTH: 282
<212> TYPE: PRT
<213> ORGANISM: Homo sapiens

<400> SEQUENCE: 1

```
Met Glu Arg Pro Ser Leu Arg Ala Leu Leu Leu Gly Ala Ala Gly Leu
1               5                   10                  15

Leu Leu Leu Leu Leu Pro Leu Ser Ser Ser Ser Ser Asp Thr Cys
                20                  25                  30

Gly Pro Cys Glu Pro Ala Ser Cys Pro Pro Leu Pro Pro Leu Gly Cys
                35                  40                  45

Leu Leu Gly Glu Thr Arg Asp Ala Cys Gly Cys Cys Pro Met Cys Ala
            50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
        115                 120                 125

Ser Gly Cys Gln Leu Arg Ala Ala Ser Gln Arg Ala Glu Ser Arg Gly
    130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
                180                 185                 190

Trp Asn Lys Val Lys Arg Gly His Tyr Gly Val Gln Arg Thr Glu Leu
            195                 200                 205

Leu Pro Gly Asp Arg Asp Asn Leu Ala Ile Gln Thr Arg Gly Gly Pro
        210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
                260                 265                 270

Pro Val Lys Lys Gly Glu Gly Ala Glu Leu
        275                 280
```

-continued

<210> SEQ ID NO 2
<211> LENGTH: 345
<212> TYPE: PRT
<213> ORGANISM: Homo sapiens

<400> SEQUENCE: 2

Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp Leu Pro Phe Ser
            20                  25                  30

Thr Val Pro Leu Lys Thr Phe Tyr Glu Pro Gly Glu Glu Ile Thr
        35                  40                  45

Tyr Ser Cys Lys Pro Gly Tyr Val Ser Arg Gly Gly Met Arg Lys Phe
50                  55                  60

Ile Cys Pro Leu Thr Gly Leu Trp Pro Ile Asn Thr Leu Lys Cys Thr
65                  70                  75                  80

Pro Arg Val Cys Pro Phe Ala Gly Ile Leu Glu Asn Gly Ala Val Arg
                85                  90                  95

Tyr Thr Thr Phe Glu Tyr Pro Asn Thr Ile Ser Phe Ser Cys Asn Thr
            100                 105                 110

Gly Phe Tyr Leu Asn Gly Ala Asp Ser Ala Lys Cys Thr Glu Gly
        115                 120                 125

Lys Trp Ser Pro Glu Leu Pro Val Cys Ala Pro Ile Ile Cys Pro Pro
130                 135                 140

Pro Ser Ile Pro Thr Phe Ala Thr Leu Arg Val Tyr Lys Pro Ser Ala
145                 150                 155                 160

Gly Asn Asn Ser Leu Tyr Arg Asp Thr Ala Val Phe Glu Cys Leu Pro
                165                 170                 175

Gln His Ala Met Phe Gly Asn Asp Thr Ile Thr Cys Thr Thr His Gly
            180                 185                 190

Asn Trp Thr Lys Leu Pro Glu Cys Arg Glu Val Lys Cys Pro Phe Pro
        195                 200                 205

Ser Arg Pro Asp Asn Gly Phe Val Asn Tyr Pro Ala Lys Pro Thr Leu
210                 215                 220

Tyr Tyr Lys Asp Lys Ala Thr Phe Gly Cys His Asp Gly Tyr Ser Leu
225                 230                 235                 240

Asp Gly Pro Glu Glu Ile Glu Cys Thr Lys Leu Gly Asn Trp Ser Ala
                245                 250                 255

Met Pro Ser Cys Lys Ala Ser Cys Lys Val Pro Val Lys Lys Ala Thr
            260                 265                 270

Val Val Tyr Gln Gly Glu Arg Val Lys Ile Gln Glu Lys Phe Lys Asn
        275                 280                 285

Gly Met Leu His Gly Asp Lys Val Ser Phe Phe Cys Lys Asn Lys Glu
290                 295                 300

Lys Lys Cys Ser Tyr Thr Glu Asp Ala Gln Cys Ile Asp Gly Thr Ile
305                 310                 315                 320

Glu Val Pro Lys Cys Phe Lys Glu His Ser Ser Leu Ala Phe Trp Lys
                325                 330                 335

Thr Asp Ala Ser Asp Val Lys Pro Cys
            340                 345

<210> SEQ ID NO 3
<211> LENGTH: 220
<212> TYPE: PRT
<213> ORGANISM: Homo sapiens

```
<400> SEQUENCE: 3

Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
            20                  25                  30

His Pro Gln Gln Ala Phe Cys Asn Ala Asp Val Val Ile Arg Ala Lys
        35                  40                  45

Ala Val Ser Glu Lys Glu Val Asp Ser Gly Asn Asp Ile Tyr Gly Asn
    50                  55                  60

Pro Ile Lys Arg Ile Gln Tyr Glu Ile Lys Gln Ile Lys Met Phe Lys
65                  70                  75                  80

Gly Pro Glu Lys Asp Ile Glu Phe Ile Tyr Thr Ala Pro Ser Ser Ala
                85                  90                  95

Val Cys Gly Val Ser Leu Asp Val Gly Gly Lys Lys Glu Tyr Leu Ile
            100                 105                 110

Ala Gly Lys Ala Glu Gly Asp Gly Lys Met His Ile Thr Leu Cys Asp
        115                 120                 125

Phe Ile Val Pro Trp Asp Thr Leu Ser Thr Thr Gln Lys Lys Ser Leu
    130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
        195                 200                 205

Pro Pro Lys Gln Glu Phe Leu Asp Ile Glu Asp Pro
    210                 215                 220

<210> SEQ ID NO 4
<211> LENGTH: 418
<212> TYPE: PRT
<213> ORGANISM: Homo sapiens

<400> SEQUENCE: 4

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140
```

```
Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
            165                 170                 175

Ala Lys Lys Gln Ile Asn Asp Tyr Val Glu Lys Gly Thr Gln Gly Lys
                180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
        210                 215                 220

Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
        370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 5
<211> LENGTH: 267
<212> TYPE: PRT
<213> ORGANISM: Homo sapiens

<400> SEQUENCE: 5

Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Ile Val Gly
            20                  25                  30

Gly Arg Arg Ala Arg Pro His Ala Trp Pro Phe Met Val Ser Leu Gln
        35                  40                  45

Leu Arg Gly Gly His Phe Cys Gly Ala Thr Leu Ile Ala Pro Asn Phe
    50                  55                  60

Val Met Ser Ala Ala His Cys Val Ala Asn Val Asn Val Arg Ala Val
65                  70                  75                  80

Arg Val Val Leu Gly Ala His Asn Leu Ser Arg Arg Glu Pro Thr Arg
                85                  90                  95
```

Gln Val Phe Ala Val Gln Arg Ile Phe Glu Asn Gly Tyr Asp Pro Val
            100                 105                 110

Asn Leu Leu Asn Asp Ile Val Ile Leu Gln Leu Asn Gly Ser Ala Thr
    115                 120                 125

Ile Asn Ala Asn Val Gln Val Ala Gln Leu Pro Ala Gln Gly Arg Arg
130                 135                 140

Leu Gly Asn Gly Val Gln Cys Leu Ala Met Gly Trp Gly Leu Leu Gly
145                 150                 155                 160

Arg Asn Arg Gly Ile Ala Ser Val Leu Gln Glu Leu Asn Val Thr Val
                165                 170                 175

Val Thr Ser Leu Cys Arg Arg Ser Asn Val Cys Thr Leu Val Arg Gly
            180                 185                 190

Arg Gln Ala Gly Val Cys Phe Gly Asp Ser Gly Ser Pro Leu Val Cys
        195                 200                 205

Asn Gly Leu Ile His Gly Ile Ala Ser Phe Val Arg Gly Gly Cys Ala
    210                 215                 220

Ser Gly Leu Tyr Pro Asp Ala Phe Ala Pro Val Ala Gln Phe Val Asn
225                 230                 235                 240

Trp Ile Asp Ser Ile Ile Gln Arg Ser Glu Asp Asn Pro Cys Pro His
                245                 250                 255

Pro Arg Asp Pro Asp Pro Ala Ser Arg Thr His
                260                 265

<210> SEQ ID NO 6
<211> LENGTH: 223
<212> TYPE: PRT
<213> ORGANISM: Homo sapiens

<400> SEQUENCE: 6

Met Asn Lys Pro Leu Leu Trp Ile Ser Val Leu Thr Ser Leu Leu Glu
1               5                   10                  15

Ala Phe Ala His Thr Asp Leu Ser Gly Lys Val Phe Val Phe Pro Arg
            20                  25                  30

Glu Ser Val Thr Asp His Val Asn Leu Ile Thr Pro Leu Glu Lys Pro
        35                  40                  45

Leu Gln Asn Phe Thr Leu Cys Phe Arg Ala Tyr Ser Asp Leu Ser Arg
    50                  55                  60

Ala Tyr Ser Leu Phe Ser Tyr Asn Thr Gln Gly Arg Asp Asn Glu Leu
65                  70                  75                  80

Leu Val Tyr Lys Glu Arg Val Gly Glu Tyr Ser Leu Tyr Ile Gly Arg
                85                  90                  95

His Lys Val Thr Ser Lys Val Ile Glu Lys Phe Pro Ala Pro Val His
            100                 105                 110

Ile Cys Val Ser Trp Glu Ser Ser Gly Ile Ala Glu Phe Trp Ile
        115                 120                 125

Asn Gly Thr Pro Leu Val Lys Lys Gly Leu Arg Gln Gly Tyr Phe Val
    130                 135                 140

Glu Ala Gln Pro Lys Ile Val Leu Gly Gln Glu Gln Asp Ser Tyr Gly
145                 150                 155                 160

Gly Lys Phe Asp Arg Ser Gln Ser Phe Val Gly Glu Ile Gly Asp Leu
                165                 170                 175

Tyr Met Trp Asp Ser Val Leu Pro Pro Glu Asn Ile Leu Ser Ala Tyr
            180                 185                 190

Gln Gly Thr Pro Leu Pro Ala Asn Ile Leu Asp Trp Gln Ala Leu Asn
        195                 200                 205

```
Tyr Glu Ile Arg Gly Tyr Val Ile Ile Lys Pro Leu Val Trp Val
    210                 215                 220

<210> SEQ ID NO 7
<211> LENGTH: 114
<212> TYPE: PRT
<213> ORGANISM: Homo sapiens

<400> SEQUENCE: 7

Met Ser Leu Pro Ser Ser Arg Ala Ala Arg Val Pro Gly Pro Ser Gly
1               5                   10                  15

Ser Leu Cys Ala Leu Leu Ala Leu Leu Leu Leu Thr Pro Pro Gly
            20                  25                  30

Pro Leu Ala Ser Ala Gly Pro Val Ser Ala Val Leu Thr Glu Leu Arg
            35                  40                  45

Cys Thr Cys Leu Arg Val Thr Leu Arg Val Asn Pro Lys Thr Ile Gly
        50                  55                  60

Lys Leu Gln Val Phe Pro Ala Gly Pro Gln Cys Ser Lys Val Glu Val
65                  70                  75                  80

Val Ala Ser Leu Lys Asn Gly Lys Gln Val Cys Leu Asp Pro Glu Ala
                85                  90                  95

Pro Phe Leu Lys Lys Val Ile Gln Lys Ile Leu Asp Ser Gly Asn Lys
            100                 105                 110

Lys Asn

<210> SEQ ID NO 8
<211> LENGTH: 119
<212> TYPE: PRT
<213> ORGANISM: Homo sapiens

<400> SEQUENCE: 8

Met Ala Gly Leu Met Thr Ile Val Thr Ser Leu Leu Phe Leu Gly Val
1               5                   10                  15

Cys Ala His His Ile Ile Pro Thr Gly Ser Val Val Ile Pro Ser Pro
            20                  25                  30

Cys Cys Met Phe Phe Val Ser Lys Arg Ile Pro Glu Asn Arg Val Val
        35                  40                  45

Ser Tyr Gln Leu Ser Ser Arg Ser Thr Cys Leu Lys Ala Gly Val Ile
    50                  55                  60

Phe Thr Thr Lys Lys Gly Gln Gln Phe Cys Gly Asp Pro Lys Gln Glu
65                  70                  75                  80

Trp Val Gln Arg Tyr Met Lys Asn Leu Asp Ala Lys Gln Lys Lys Ala
                85                  90                  95

Ser Pro Arg Ala Arg Ala Val Ala Val Lys Gly Pro Val Gln Arg Tyr
            100                 105                 110

Pro Gly Asn Gln Thr Thr Cys
        115

<210> SEQ ID NO 9
<211> LENGTH: 467
<212> TYPE: PRT
<213> ORGANISM: Homo sapiens

<400> SEQUENCE: 9

Met Phe Ser Leu Lys Thr Leu Pro Phe Leu Leu Leu Leu His Val Gln
1               5                   10                  15

Ile Ser Lys Ala Phe Pro Val Ser Ser Lys Glu Lys Asn Thr Lys Thr
```

```
                20                  25                  30
    Val Gln Asp Tyr Leu Glu Lys Phe Tyr Gln Leu Pro Ser Asn Gln Tyr
                    35                  40                  45
    Gln Ser Thr Arg Lys Asn Gly Thr Asn Val Ile Val Glu Lys Leu Lys
     50                  55                  60
    Glu Met Gln Arg Phe Phe Gly Leu Asn Val Thr Gly Lys Pro Asn Glu
     65                  70                  75                  80
    Glu Thr Leu Asp Met Met Lys Lys Pro Arg Cys Gly Val Pro Asp Ser
                     85                  90                  95
    Gly Gly Phe Met Leu Thr Pro Gly Asn Pro Lys Trp Glu Arg Thr Asn
                    100                 105                 110
    Leu Thr Tyr Arg Ile Arg Asn Tyr Thr Pro Gln Leu Ser Glu Ala Glu
                    115                 120                 125
    Val Glu Arg Ala Ile Lys Asp Ala Phe Glu Leu Trp Ser Val Ala Ser
                    130                 135                 140
    Pro Leu Ile Phe Thr Arg Ile Ser Gln Gly Glu Ala Asp Ile Asn Ile
    145                 150                 155                 160
    Ala Phe Tyr Gln Arg Asp His Gly Asp Asn Ser Pro Phe Asp Gly Pro
                    165                 170                 175
    Asn Gly Ile Leu Ala His Ala Phe Gln Pro Gly Gln Gly Ile Gly Gly
                    180                 185                 190
    Asp Ala His Phe Asp Ala Glu Glu Thr Trp Thr Asn Thr Ser Ala Asn
                    195                 200                 205
    Tyr Asn Leu Phe Leu Val Ala Ala His Glu Phe Gly His Ser Leu Gly
                    210                 215                 220
    Leu Ala His Ser Ser Asp Pro Gly Ala Leu Met Tyr Pro Asn Tyr Ala
    225                 230                 235                 240
    Phe Arg Glu Thr Ser Asn Tyr Ser Leu Pro Gln Asp Asp Ile Asp Gly
                    245                 250                 255
    Ile Gln Ala Ile Tyr Gly Leu Ser Ser Asn Pro Ile Gln Pro Thr Gly
                    260                 265                 270
    Pro Ser Thr Pro Lys Pro Cys Asp Pro Ser Leu Thr Phe Asp Ala Ile
                    275                 280                 285
    Thr Thr Leu Arg Gly Glu Ile Leu Phe Phe Lys Asp Arg Tyr Phe Trp
    290                 295                 300
    Arg Arg His Pro Gln Leu Gln Arg Val Glu Met Asn Phe Ile Ser Leu
    305                 310                 315                 320
    Phe Trp Pro Ser Leu Pro Thr Gly Ile Gln Ala Ala Tyr Glu Asp Phe
                    325                 330                 335
    Asp Arg Asp Leu Ile Phe Leu Phe Lys Gly Asn Gln Tyr Trp Ala Leu
                    340                 345                 350
    Ser Gly Tyr Asp Ile Leu Gln Gly Tyr Pro Lys Asp Ile Ser Asn Tyr
                    355                 360                 365
    Gly Phe Pro Ser Ser Val Gln Ala Ile Asp Ala Ala Val Phe Tyr Arg
                    370                 375                 380
    Ser Lys Thr Tyr Phe Phe Val Asn Asp Gln Phe Trp Arg Tyr Asp Asn
    385                 390                 395                 400
    Gln Arg Gln Phe Met Glu Pro Gly Tyr Pro Lys Ser Ile Ser Gly Ala
                    405                 410                 415
    Phe Pro Gly Ile Glu Ser Lys Val Asp Ala Val Phe Gln Gln Glu His
                    420                 425                 430
    Phe Phe His Val Phe Ser Gly Pro Arg Tyr Tyr Ala Phe Asp Leu Ile
                    435                 440                 445
```

-continued

Ala Gln Arg Val Thr Arg Val Ala Arg Gly Asn Lys Trp Leu Asn Cys
        450                 455                 460

Arg Tyr Gly
465

<210> SEQ ID NO 10
<211> LENGTH: 412
<212> TYPE: PRT
<213> ORGANISM: Homo sapiens

<400> SEQUENCE: 10

Met Gln Pro Ser Ser Leu Leu Pro Leu Ala Leu Cys Leu Leu Ala Ala
1               5                   10                  15

Pro Ala Ser Ala Leu Val Arg Ile Pro Leu His Lys Phe Thr Ser Ile
            20                  25                  30

Arg Arg Thr Met Ser Glu Val Gly Gly Ser Val Glu Asp Leu Ile Ala
        35                  40                  45

Lys Gly Pro Val Ser Lys Tyr Ser Gln Ala Val Pro Ala Val Thr Glu
    50                  55                  60

Gly Pro Ile Pro Glu Val Leu Lys Asn Tyr Met Asp Ala Gln Tyr Tyr
65                  70                  75                  80

Gly Glu Ile Gly Ile Gly Thr Pro Pro Gln Cys Phe Thr Val Val Phe
                85                  90                  95

Asp Thr Gly Ser Ser Asn Leu Trp Val Pro Ser Ile His Cys Lys Leu
            100                 105                 110

Leu Asp Ile Ala Cys Trp Ile His His Lys Tyr Asn Ser Asp Lys Ser
        115                 120                 125

Ser Thr Tyr Val Lys Asn Gly Thr Ser Phe Asp Ile His Tyr Gly Ser
    130                 135                 140

Gly Ser Leu Ser Gly Tyr Leu Ser Gln Asp Thr Val Ser Val Pro Cys
145                 150                 155                 160

Gln Ser Ala Ser Ser Ala Ser Ala Leu Gly Gly Val Lys Val Glu Arg
                165                 170                 175

Gln Val Phe Gly Glu Ala Thr Lys Gln Pro Gly Ile Thr Phe Ile Ala
            180                 185                 190

Ala Lys Phe Asp Gly Ile Leu Gly Met Ala Tyr Pro Arg Ile Ser Val
        195                 200                 205

Asn Asn Val Leu Pro Val Phe Asp Asn Leu Met Gln Gln Lys Leu Val
    210                 215                 220

Asp Gln Asn Ile Phe Ser Phe Tyr Leu Ser Arg Asp Pro Asp Ala Gln
225                 230                 235                 240

Pro Gly Gly Glu Leu Met Leu Gly Gly Thr Asp Ser Lys Tyr Tyr Lys
                245                 250                 255

Gly Ser Leu Ser Tyr Leu Asn Val Thr Arg Lys Ala Tyr Trp Gln Val
            260                 265                 270

His Leu Asp Gln Val Glu Val Ala Ser Gly Leu Thr Leu Cys Lys Glu
        275                 280                 285

Gly Cys Glu Ala Ile Val Asp Thr Gly Thr Ser Leu Met Val Gly Pro
    290                 295                 300

Val Asp Glu Val Arg Glu Leu Gln Lys Ala Ile Gly Ala Val Pro Leu
305                 310                 315                 320

Ile Gln Gly Glu Tyr Met Ile Pro Cys Glu Lys Val Ser Thr Leu Pro
                325                 330                 335

Ala Ile Thr Leu Lys Leu Gly Gly Lys Gly Tyr Lys Leu Ser Pro Glu

```
                340             345             350
Asp Tyr Thr Leu Lys Val Ser Gln Ala Gly Lys Thr Leu Cys Leu Ser
        355                 360                 365

Gly Phe Met Gly Met Asp Ile Pro Pro Ser Gly Pro Leu Trp Ile
    370                 375                 380

Leu Gly Asp Val Phe Ile Gly Arg Tyr Tyr Thr Val Phe Asp Arg Asp
385                 390                 395                 400

Asn Asn Arg Val Gly Phe Ala Glu Ala Ala Arg Leu
                405                 410

<210> SEQ ID NO 11
<211> LENGTH: 109
<212> TYPE: PRT
<213> ORGANISM: Homo sapiens

<400> SEQUENCE: 11

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
                20                  25                  30

Cys Arg Cys Val Gln Glu Ser Ser Val Phe Ile Pro Arg Arg Phe Ile
            35                  40                  45

Asp Arg Ile Gln Ile Leu Pro Arg Gly Asn Gly Cys Pro Arg Lys Glu
        50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
                100                 105

<210> SEQ ID NO 12
<211> LENGTH: 585
<212> TYPE: PRT
<213> ORGANISM: Homo sapiens

<400> SEQUENCE: 12

Met Ser Gln Gln His Thr Leu Pro Val Thr Leu Ser Pro Ala Leu Ser
1               5                   10                  15

Gln Glu Leu Leu Lys Thr Val Pro Pro Val Asn Thr His Gln Glu
                20                  25                  30

Gln Met Lys Gln Pro Thr Pro Leu Pro Pro Cys Gln Lys Val Pro
            35                  40                  45

Val Glu Leu Pro Val Glu Val Pro Ser Lys Gln Glu Glu Lys His Met
        50                  55                  60

Thr Ala Val Lys Gly Leu Pro Glu Gln Glu Cys Gln Gln Gln Lys
65                  70                  75                  80

Glu Pro Gln Glu Gln Leu Gln Gln His Trp Glu Gln His Glu
                85                  90                  95

Glu Tyr Gln Lys Ala Glu Asn Pro Glu Gln Gln Leu Lys Glu Lys
                100                 105                 110

Thr Gln Arg Asp Gln Gln Leu Asn Lys Gln Leu Glu Glu Lys Lys
            115                 120                 125

Leu Leu Asp Gln Gln Leu Asp Gln Glu Leu Val Lys Arg Asp Glu Gln
        130                 135                 140

Leu Gly Met Lys Lys Glu Gln Leu Leu Glu Leu Pro Glu Gln Gln Glu
```

```
            145                 150                 155                 160
Gly His Leu Lys His Leu Glu Gln Gln Glu Gly Gln Leu Lys His Pro
                    165                 170                 175
Glu Gln Gln Glu Gly Gln Leu Glu Leu Pro Glu Gln Gln Gly Gln
                    180                 185                 190
Leu Glu Leu Pro Glu Gln Gln Gly Gln Leu Glu Leu Pro Glu Gln
                    195                 200                 205
Gln Glu Gly Gln Leu Glu Leu Pro Glu Gln Gln Gly Gln Leu Glu
                    210                 215                 220
Leu Pro Glu Gln Gln Glu Gly Gln Leu Glu Leu Pro Gln Gln Glu
225                 230                 235                 240
Gly Gln Leu Glu Leu Ser Glu Gln Gln Glu Gly Gln Leu Glu Leu Ser
                    245                 250                 255
Glu Gln Gln Glu Gly Gln Leu Lys His Leu Glu His Gln Glu Gly Gln
                    260                 265                 270
Leu Glu Val Pro Glu Glu Gln Met Gly Gln Leu Lys Tyr Leu Glu Gln
                    275                 280                 285
Gln Glu Gly Gln Leu Lys His Leu Asp Gln Gln Glu Lys Gln Pro Glu
                    290                 295                 300
Leu Pro Glu Gln Gln Met Gly Gln Leu Lys His Leu Glu Gln Gln Glu
305                 310                 315                 320
Gly Gln Pro Lys His Leu Glu Gln Gln Glu Gly Gln Leu Glu Gln Leu
                    325                 330                 335
Glu Glu Gln Glu Gly Gln Leu Lys His Leu Glu Gln Gln Glu Gly Gln
                    340                 345                 350
Leu Glu His Leu Glu His Gln Glu Gly Gln Leu Gly Leu Pro Glu Gln
                    355                 360                 365
Gln Val Leu Gln Leu Lys Gln Leu Glu Lys Gln Gly Gln Pro Lys
                    370                 375                 380
His Leu Glu Glu Glu Gly Gln Leu Lys His Leu Val Gln Gln Glu
385                 390                 395                 400
Gly Gln Leu Lys His Leu Val Gln Gln Glu Gly Gln Leu Glu Gln Gln
                    405                 410                 415
Glu Arg Gln Val Glu His Leu Glu Gln Gln Val Gly Gln Leu Lys His
                    420                 425                 430
Leu Glu Glu Gln Glu Gly Gln Leu Lys His Leu Glu Gln Gln Gln Gly
                    435                 440                 445
Gln Leu Glu Val Pro Glu Gln Gln Val Gly Gln Pro Lys Asn Leu Glu
                    450                 455                 460
Gln Glu Glu Lys Gln Leu Glu Leu Pro Glu Gln Gln Glu Gly Gln Val
465                 470                 475                 480
Lys His Leu Glu Lys Gln Glu Ala Gln Leu Glu Leu Pro Glu Gln Gln
                    485                 490                 495
Val Gly Gln Pro Lys His Leu Glu Gln Gln Glu Lys His Leu Glu His
                    500                 505                 510
Pro Glu Gln Gln Asp Gly Gln Leu Lys His Leu Glu Gln Gln Glu Gly
             515                 520                 525
Gln Leu Lys Asp Leu Glu Gln Gln Lys Gly Gln Leu Glu Gln Pro Val
             530                 535                 540
Phe Ala Pro Ala Pro Gly Gln Val Gln Asp Ile Gln Pro Ala Leu Pro
545                 550                 555                 560
Thr Lys Gly Glu Val Leu Leu Pro Val Glu His Gln Gln Gln Lys Gln
             565                 570                 575
```

<210> SEQ ID NO 13
<211> LENGTH: 918
<212> TYPE: PRT
<213> ORGANISM: Homo sapiens

<400> SEQUENCE: 13

```
Glu Val Gln Trp Pro Pro Lys His Lys
            580             585

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
```

```
                    355                 360                 365
        Thr Leu Thr Arg Trp Lys Ser His Leu Gln Asn Tyr Thr Val Asn Ala
        370                 375                 380

Thr Lys Leu Thr Val Asn Leu Thr Asn Asp Arg Tyr Leu Ala Thr Leu
        385                 390                 395                 400

Thr Val Arg Asn Leu Val Gly Lys Ser Asp Ala Ala Val Leu Thr Ile
                        405                 410                 415

Pro Ala Cys Asp Phe Gln Ala Thr His Pro Val Met Asp Leu Lys Ala
                    420                 425                 430

Phe Pro Lys Asp Asn Met Leu Trp Val Glu Trp Thr Thr Pro Arg Glu
                435                 440                 445

Ser Val Lys Lys Tyr Ile Leu Glu Trp Cys Val Leu Ser Asp Lys Ala
        450                 455                 460

Pro Cys Ile Thr Asp Trp Gln Gln Glu Asp Gly Thr Val His Arg Thr
        465                 470                 475                 480

Tyr Leu Arg Gly Asn Leu Ala Glu Ser Lys Cys Tyr Leu Ile Thr Val
                        485                 490                 495

Thr Pro Val Tyr Ala Asp Gly Pro Gly Ser Pro Glu Ser Ile Lys Ala
                    500                 505                 510

Tyr Leu Lys Gln Ala Pro Pro Ser Lys Gly Pro Thr Val Arg Thr Lys
                515                 520                 525

Lys Val Gly Lys Asn Glu Ala Val Leu Glu Trp Asp Gln Leu Pro Val
        530                 535                 540

Asp Val Gln Asn Gly Phe Ile Arg Asn Tyr Thr Ile Phe Tyr Arg Thr
        545                 550                 555                 560

Ile Ile Gly Asn Glu Thr Ala Val Asn Val Asp Ser Ser His Thr Glu
                        565                 570                 575

Tyr Thr Leu Ser Ser Leu Thr Ser Asp Thr Leu Tyr Met Val Arg Met
                    580                 585                 590

Ala Ala Tyr Thr Asp Glu Gly Gly Lys Asp Gly Pro Glu Phe Thr Phe
                595                 600                 605

Thr Thr Pro Lys Phe Ala Gln Gly Glu Ile Glu Ala Ile Val Val Pro
        610                 615                 620

Val Cys Leu Ala Phe Leu Leu Thr Thr Leu Leu Gly Val Leu Phe Cys
        625                 630                 635                 640

Phe Asn Lys Arg Asp Leu Ile Lys Lys His Ile Trp Pro Asn Val Pro
                        645                 650                 655

Asp Pro Ser Lys Ser His Ile Ala Gln Trp Ser Pro His Thr Pro Pro
                    660                 665                 670

Arg His Asn Phe Asn Ser Lys Asp Gln Met Tyr Ser Asp Gly Asn Phe
                675                 680                 685

Thr Asp Val Ser Val Val Glu Ile Glu Ala Asn Asp Lys Lys Pro Phe
        690                 695                 700

Pro Glu Asp Leu Lys Ser Leu Asp Leu Phe Lys Lys Glu Lys Ile Asn
        705                 710                 715                 720

Thr Glu Gly His Ser Ser Gly Ile Gly Gly Ser Ser Cys Met Ser Ser
                        725                 730                 735

Ser Arg Pro Ser Ile Ser Ser Ser Asp Glu Asn Glu Ser Ser Gln Asn
                    740                 745                 750

Thr Ser Ser Thr Val Gln Tyr Ser Thr Val Val His Ser Gly Tyr Arg
                755                 760                 765

His Gln Val Pro Ser Val Gln Val Phe Ser Arg Ser Glu Ser Thr Gln
        770                 775                 780
```

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
            805                 810                 815

Gln Asn Cys Ser Gln His Glu Ser Ser Pro Asp Ile Ser His Phe Glu
        820                 825                 830

Arg Ser Lys Gln Val Ser Ser Val Asn Glu Glu Asp Phe Val Arg Leu
    835                 840                 845

Lys Gln Gln Ile Ser Asp His Ile Ser Gln Ser Cys Gly Ser Gly Gln
850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915

<210> SEQ ID NO 14
<211> LENGTH: 5
<212> TYPE: PRT
<213> ORGANISM: Homo sapiens

<400> SEQUENCE: 14

Arg Pro Ser Lys Ala
1               5

<210> SEQ ID NO 15
<211> LENGTH: 5
<212> TYPE: PRT
<213> ORGANISM: Homo sapiens

<400> SEQUENCE: 15

Asn Ile Ala Ser Phe
1               5

<210> SEQ ID NO 16
<211> LENGTH: 728
<212> TYPE: PRT
<213> ORGANISM: Homo sapiens

<400> SEQUENCE: 16

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

-continued

Gly His Glu Phe Asp Leu Tyr Glu Asn Lys Asp Tyr Ile Arg Asn Cys
            115                 120                 125
Ile Ile Gly Lys Gly Arg Ser Tyr Lys Gly Thr Val Ser Ile Thr Lys
        130                 135                 140
Ser Gly Ile Lys Cys Gln Pro Trp Ser Ser Met Ile Pro His Glu His
145                 150                 155                 160
Ser Phe Leu Pro Ser Ser Tyr Arg Gly Lys Asp Leu Gln Glu Asn Tyr
                165                 170                 175
Cys Arg Asn Pro Arg Gly Glu Glu Gly Pro Trp Cys Phe Thr Ser
                180                 185                 190
Asn Pro Glu Val Arg Tyr Glu Val Cys Asp Ile Pro Gln Cys Ser Glu
                195                 200                 205
Val Glu Cys Met Thr Cys Asn Gly Glu Ser Tyr Arg Gly Leu Met Asp
        210                 215                 220
His Thr Glu Ser Gly Lys Ile Cys Gln Arg Trp Asp His Gln Thr Pro
225                 230                 235                 240
His Arg His Lys Phe Leu Pro Glu Arg Tyr Pro Asp Lys Gly Phe Asp
                245                 250                 255
Asp Asn Tyr Cys Arg Asn Pro Asp Gly Gln Pro Arg Pro Trp Cys Tyr
                260                 265                 270
Thr Leu Asp Pro His Thr Arg Trp Glu Tyr Cys Ala Ile Lys Thr Cys
        275                 280                 285
Ala Asp Asn Thr Met Asn Asp Thr Asp Val Pro Leu Glu Thr Thr Glu
        290                 295                 300
Cys Ile Gln Gly Gln Gly Glu Gly Tyr Arg Gly Thr Val Asn Thr Ile
305                 310                 315                 320
Trp Asn Gly Ile Pro Cys Gln Arg Trp Asp Ser Gln Tyr Pro His Glu
                325                 330                 335
His Asp Met Thr Pro Glu Asn Phe Lys Cys Lys Asp Leu Arg Glu Asn
                340                 345                 350
Tyr Cys Arg Asn Pro Asp Gly Ser Glu Ser Pro Trp Cys Phe Thr Thr
        355                 360                 365
Asp Pro Asn Ile Arg Val Gly Tyr Cys Ser Gln Ile Pro Asn Cys Asp
        370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
                420                 425                 430
Ser Lys Leu Asn Glu Asn Tyr Cys Arg Asn Pro Asp Asp Asp Ala His
                435                 440                 445
Gly Pro Trp Cys Tyr Thr Gly Asn Pro Leu Ile Pro Trp Asp Tyr Cys
        450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
                500                 505                 510
Tyr Arg Asn Lys His Ile Cys Gly Gly Ser Leu Ile Lys Glu Ser Trp
                515                 520                 525
Val Leu Thr Ala Arg Gln Cys Phe Pro Ser Arg Asp Leu Lys Asp Tyr

-continued

```
                530             535             540
Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
                580                 585                 590

Phe Val Ser Thr Ile Asp Leu Pro Asn Tyr Gly Cys Thr Ile Pro Glu
                595                 600                 605

Lys Thr Ser Cys Ser Val Tyr Gly Trp Gly Tyr Thr Gly Leu Ile Asn
                610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
                675                 680                 685

Gly Val Ile Val Pro Gly Arg Gly Cys Ala Ile Pro Asn Arg Pro Gly
                690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 17
<211> LENGTH: 224
<212> TYPE: PRT
<213> ORGANISM: Homo sapiens

<400> SEQUENCE: 17

Met Pro Gly Ser Pro Arg Pro Ala Pro Ser Trp Val Leu Leu Leu Arg
1                   5                   10                  15

Leu Leu Ala Leu Leu Arg Pro Pro Gly Leu Gly Glu Ala Cys Ser Cys
                20                  25                  30

Ala Pro Ala His Pro Gln Gln His Ile Cys His Ser Ala Leu Val Ile
                35                  40                  45

Arg Ala Lys Ile Ser Ser Glu Lys Val Val Pro Ala Ser Ala Asp Pro
50                  55                  60

Ala Asp Thr Glu Lys Met Leu Arg Tyr Glu Ile Lys Gln Ile Lys Met
65                  70                  75                  80

Phe Lys Gly Phe Glu Lys Val Lys Asp Val Gln Tyr Ile Tyr Thr Pro
                85                  90                  95

Phe Asp Ser Ser Leu Cys Gly Val Lys Leu Glu Ala Asn Ser Gln Lys
                100                 105                 110

Gln Tyr Leu Leu Thr Gly Gln Val Leu Ser Asp Gly Lys Val Phe Ile
                115                 120                 125

His Leu Cys Asn Tyr Ile Glu Pro Trp Glu Asp Leu Ser Leu Val Gln
                130                 135                 140

Arg Glu Ser Leu Asn His His Tyr His Leu Asn Cys Gly Cys Gln Ile
145                 150                 155                 160

Thr Thr Cys Tyr Thr Val Pro Cys Thr Ile Ser Ala Pro Asn Glu Cys
                165                 170                 175
```

Leu Trp Thr Asp Trp Leu Leu Glu Arg Lys Leu Tyr Gly Tyr Gln Ala
            180                 185                 190

Gln His Tyr Val Cys Met Lys His Val Asp Gly Thr Cys Ser Trp Tyr
        195                 200                 205

Arg Gly His Leu Pro Leu Arg Lys Glu Phe Val Asp Ile Val Gln Pro
    210                 215                 220

<210> SEQ ID NO 18
<211> LENGTH: 89
<212> TYPE: PRT
<213> ORGANISM: Homo sapiens

<400> SEQUENCE: 18

Met Lys Gly Leu Ala Ala Leu Leu Val Leu Val Cys Thr Met Ala
1               5                   10                  15

Leu Cys Ser Cys Ala Gln Val Gly Thr Asn Lys Glu Leu Cys Cys Leu
                20                  25                  30

Val Tyr Thr Ser Trp Gln Ile Pro Gln Lys Phe Ile Val Asp Tyr Ser
            35                  40                  45

Glu Thr Ser Pro Gln Cys Pro Lys Pro Gly Val Ile Leu Leu Thr Lys
    50                  55                  60

Arg Gly Arg Gln Ile Cys Ala Asp Pro Asn Lys Lys Trp Val Gln Lys
65                  70                  75                  80

Tyr Ile Ser Asp Leu Lys Leu Asn Ala
                85

<210> SEQ ID NO 19
<211> LENGTH: 267
<212> TYPE: PRT
<213> ORGANISM: Homo sapiens

<400> SEQUENCE: 19

Met Arg Leu Thr Val Leu Cys Ala Val Cys Leu Leu Pro Gly Ser Leu
1               5                   10                  15

Ala Leu Pro Leu Pro Gln Glu Ala Gly Gly Met Ser Glu Leu Gln Trp
                20                  25                  30

Glu Gln Ala Gln Asp Tyr Leu Lys Arg Phe Tyr Leu Tyr Asp Ser Glu
            35                  40                  45

Thr Lys Asn Ala Asn Ser Leu Glu Ala Lys Leu Lys Glu Met Gln Lys
    50                  55                  60

Phe Phe Gly Leu Pro Ile Thr Gly Met Leu Asn Ser Arg Val Ile Glu
65                  70                  75                  80

Ile Met Gln Lys Pro Arg Cys Gly Val Pro Asp Val Ala Glu Tyr Ser
                85                  90                  95

Leu Phe Pro Asn Ser Pro Lys Trp Thr Ser Lys Val Val Thr Tyr Arg
                100                 105                 110

Ile Val Ser Tyr Thr Arg Asp Leu Pro His Ile Thr Val Asp Arg Leu
            115                 120                 125

Val Ser Lys Ala Leu Asn Met Trp Gly Lys Glu Ile Pro Leu His Phe
    130                 135                 140

Arg Lys Val Val Trp Gly Thr Ala Asp Ile Met Ile Gly Phe Ala Arg
145                 150                 155                 160

Gly Ala His Gly Asp Ser Tyr Pro Phe Asp Gly Pro Gly Asn Thr Leu
                165                 170                 175

Ala His Ala Phe Ala Pro Gly Thr Gly Leu Gly Gly Asp Ala His Phe
            180                 185                 190

Asp Glu Asp Glu Arg Trp Thr Asp Gly Ser Ser Leu Gly Ile Asn Phe
            195                 200                 205

Leu Tyr Ala Ala Thr His Glu Leu Gly His Ser Leu Gly Met Gly His
    210                 215                 220

Ser Ser Asp Pro Asn Ala Val Met Tyr Pro Thr Tyr Gly Asn Gly Asp
225                 230                 235                 240

Pro Gln Asn Phe Lys Leu Ser Gln Asp Ile Lys Gly Ile Gln Lys
                245                 250                 255

Leu Tyr Gly Lys Arg Ser Asn Ser Arg Lys Lys
                260                 265

<210> SEQ ID NO 20
<211> LENGTH: 94
<212> TYPE: PRT
<213> ORGANISM: Homo sapiens

<400> SEQUENCE: 20

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
                20                  25                  30

Ile Gly Pro Gly Val Lys Ala Val Lys Val Ala Asp Ile Glu Lys Ala
            35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90

<210> SEQ ID NO 21
<211> LENGTH: 107
<212> TYPE: PRT
<213> ORGANISM: Homo sapiens

<400> SEQUENCE: 21

Met Ala Arg Ala Ala Leu Ser Ala Ala Pro Ser Asn Pro Arg Leu Leu
1               5                   10                  15

Arg Val Ala Leu Leu Leu Leu Leu Leu Val Ala Ala Gly Arg Arg Ala
                20                  25                  30

Ala Gly Ala Ser Val Ala Thr Glu Leu Arg Cys Gln Cys Leu Gln Thr
            35                  40                  45

Leu Gln Gly Ile His Pro Lys Asn Ile Gln Ser Val Asn Val Lys Ser
    50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
            100                 105

<210> SEQ ID NO 22
<211> LENGTH: 107
<212> TYPE: PRT
<213> ORGANISM: Homo sapiens

<400> SEQUENCE: 22

Met Ala Arg Ala Thr Leu Ser Ala Ala Pro Ser Asn Pro Arg Leu Leu

```
                1               5                   10                  15
            Arg Val Ala Leu Leu Leu Leu Leu Val Ala Ala Ser Arg Arg Ala
                            20                  25                  30

Ala Gly Ala Pro Leu Ala Thr Glu Leu Arg Cys Gln Cys Leu Gln Thr
                            35                  40                  45

Leu Gln Gly Ile His Leu Lys Asn Ile Gln Ser Val Lys Val Lys Ser
                        50                  55                  60

Pro Gly Pro His Cys Ala Gln Thr Glu Val Ile Ala Thr Leu Lys Asn
            65                  70                  75                  80

Gly Gln Lys Ala Cys Leu Asn Pro Ala Ser Pro Met Val Lys Lys Ile
                            85                  90                  95

Ile Glu Lys Met Leu Lys Asn Gly Lys Ser Asn
                            100                 105

<210> SEQ ID NO 23
<211> LENGTH: 107
<212> TYPE: PRT
<213> ORGANISM: Homo sapiens

<400> SEQUENCE: 23

Met Ala His Ala Thr Leu Ser Ala Ala Pro Ser Asn Pro Arg Leu Leu
            1               5                   10                  15

Arg Val Ala Leu Leu Leu Leu Leu Val Ala Ala Ser Arg Arg Ala
                            20                  25                  30

Ala Gly Ala Ser Val Val Thr Glu Leu Arg Cys Gln Cys Leu Gln Thr
                            35                  40                  45

Leu Gln Gly Ile His Leu Lys Asn Ile Gln Ser Val Asn Val Arg Ser
                        50                  55                  60

Pro Gly Pro His Cys Ala Gln Thr Glu Val Ile Ala Thr Leu Lys Asn
            65                  70                  75                  80

Gly Lys Lys Ala Cys Leu Asn Pro Ala Ser Pro Met Val Gln Lys Ile
                            85                  90                  95

Ile Glu Lys Ile Leu Asn Lys Gly Ser Thr Asn
                            100                 105

<210> SEQ ID NO 24
<211> LENGTH: 132
<212> TYPE: PRT
<213> ORGANISM: Homo sapiens

<400> SEQUENCE: 24

Met Lys Ser Ser Gly Leu Phe Pro Phe Leu Val Leu Leu Ala Leu Gly
            1               5                   10                  15

Thr Leu Ala Pro Trp Ala Val Glu Gly Ser Gly Lys Ser Phe Lys Ala
                            20                  25                  30

Gly Val Cys Pro Pro Lys Lys Ser Ala Gln Cys Leu Arg Tyr Lys Lys
                            35                  40                  45

Pro Glu Cys Gln Ser Asp Trp Gln Cys Pro Gly Lys Lys Arg Cys Cys
                        50                  55                  60

Pro Asp Thr Cys Gly Ile Lys Cys Leu Asp Pro Val Asp Thr Pro Asn
            65                  70                  75                  80

Pro Thr Arg Arg Lys Pro Gly Lys Cys Pro Val Thr Tyr Gly Gln Cys
                            85                  90                  95

Leu Met Leu Asn Pro Pro Asn Phe Cys Glu Met Asp Gly Gln Cys Lys
                            100                 105                 110

Arg Asp Leu Lys Cys Cys Met Gly Met Cys Gly Lys Ser Cys Val Ser
```

```
            115                 120                 125
Pro Val Lys Ala
    130
```

METHODS FOR DIAGNOSIS AND PROGNOSIS OF RENAL INJURY AND RENAL FAILURE USING INSULIN-LIKE GROWTH FACTOR-BINDING PROTEIN 7 AND METALLOPROTEINASE INHIBITOR 2

The present invention is filed under 35 U.S.C. § 371 as the U.S. national phase of International Application No. PCT/US2012/068498, filed Dec. 7, 2012, which designated the U.S. and claims priority to U.S. Provisional Patent Application 61/568,447, filed Dec. 8, 2011, and to U.S. Provisional Patent Application 61/593,561, filed Feb. 1, 2012, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Sep. 5, 2014, is named ASTS0009US_SequenceListing.txt and is 55 kilobytes in size.

BACKGROUND OF THE INVENTION

The following discussion of the background of the invention is merely provided to aid the reader in understanding the invention and is not admitted to describe or constitute prior art to the present invention.

The term "sepsis" has been used to describe a variety of clinical conditions related to systemic manifestations of inflammation accompanied by an infection. Because of clinical similarities to inflammatory responses secondary to non-infectious etiologies, identifying sepsis has been a particularly challenging diagnostic problem. Recently, the American College of Chest Physicians and the American Society of Critical Care Medicine (Bone et al., *Chest* 101: 1644-53, 1992) published definitions for "Systemic Inflammatory Response Syndrome" (or "SIRS"), which refers generally to a severe systemic response to an infectious or non-infectious insult, and for the related syndromes "sepsis," "severe sepsis," and "septic shock," and extending to multiple organ dysfunction syndrome ("MODS"). These definitions, described below, are intended for each of these phrases for the purposes of the present application.

"SIRS" refers to a condition that exhibits two or more of the following:
a temperature>38° C. or <36° C.;
a heart rate of >90 beats per minute (tachycardia);
a respiratory rate of >20 breaths per minute (tachypnea) or a $P_aCO_2$<4.3 kPa; and
a white blood cell count >12,000 per $mm^3$, <4,000 per $mm^3$, or >10% immature (band) forms.

"Sepsis" refers to SIRS, further accompanied by a clinically evident or microbiologically confirmed infection. This infection may be bacterial, fungal, parasitic, or viral.

"Severe sepsis" refers to a subset of sepsis patients, in which sepsis is further accompanied by organ hypoperfusion made evident by at least one sign of organ dysfunction such as hypoxemia, oliguria, metabolic acidosis, or altered cerebral function.

"Septic shock" refers to a subset of severe sepsis patients, in which severe sepsis is further accompanied by hypotension, made evident by a systolic blood pressure <90 mm Hg, or the requirement for pharmaceutical intervention to maintain blood pressure.

MODS (multiple organ dysfunction syndrome) is the presence of altered organ function in a patient who is acutely ill such that homeostasis cannot be maintained without intervention. Primary MODS is the direct result of a well-defined insult in which organ dysfunction occurs early and can be directly attributable to the insult itself. Secondary MODS develops as a consequence of a host response and is identified within the context of SIRS.

A systemic inflammatory response leading to a diagnosis of SIRS may be related to both infection and to numerous non-infective etiologies, including burns, pancreatitis, trauma, heat stroke, and neoplasia. While conceptually it may be relatively simple to distinguish between sepsis and non-septic SIRS, no diagnostic tools have been described to unambiguously distinguish these related conditions. See, e.g., Llewelyn and Cohen, *Int. Care Med.* 27: S10-S32, 2001. For example, because more than 90% of sepsis cases involve bacterial infection, the "gold standard" for confirming infection has been microbial growth from blood, urine, pleural fluid, cerebrospinal fluid, peritoneal fluid, synnovial fluid, sputum, or other tissue specimens. Such culture has been reported, however, to fail to confirm 50% or more of patients exhibiting strong clinical evidence of sepsis. See, e.g., Jaimes et al., *Int. Care Med* 29: 1368-71, published electronically Jun. 26, 2003.

Development of acute kidney injury (AKI) during sepsis increases patient morbidity, predicts higher mortality, has a significant effect on multiple organ functions, is associated with an increased length of stay in the intensive care unit, and hence consumes considerable healthcare resources. Several authors have noted that, when compared with AKI of nonseptic origin, septic AKI is characterized by a distinct pathophysiology and therefore requires a different approach. Sepsis-related AKI has been described in terms of elevated and imbalanced pro- and anti-inflammatory mediators (the so-called "peak concentration hypothesis"), coupled with severe endothelial dysfunction and a perturbed coagulation cascade operate synergistically to induce chemically and biologically mediated kidney injury. Major impediments to progress in understanding, early diagnosis, and application of appropriate therapeutic modalities in sepsis-induced AKI include limited histopathologic information, few animal models that closely mimic human sepsis, and a relative shortage of specific diagnostic tools. See, e.g., Zarjou and Agarwal, *J. Am. Soc. Nephrol.* 22: 999-1006, 2011; Ronco et al., *Clin. J. Am. Soc. Nephrol.* 3: 531-44, 2008.

These limitations underscore the need for better methods to evaluate sepsis patients in order to identify those most at risk for AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a sepsis patient diagnosed with sepsis. As described herein, measurement of one or more biomarkers selected from the group consisting of Insulin-like growth factor-binding protein 7, Beta-2-glycoprotein 1, Metalloproteinase inhibitor 2, Alpha-1 Antitrypsin, Leukocyte elastase, Serum Amyloid P Component, C-X-C motif chemokine 6, Immunoglobulin A, Immunoglobulin G subclass I, C-C motif chemokine 24, Neutrophil collagenase, Cathepsin D, C-X-C motif chemokine 13, Involucrin, Interleukin-6 receptor subunit beta, Hepatocyte Growth Factor, CXCL-1, -2, -3, Immunoglobulin G subclass II, Metalloproteinase inhibitor 4, C-C motif chemokine 18, Matrilysin, C-X-C motif chemokine 11, and Antileukoproteinase (referred to herein as a "kidney injury marker") can be used for diagnosis, prognosis, risk stratification, staging, monitoring, categorizing and determination of further diagnosis and treatment regimens in sepsis patients.

The kidney injury markers of the present invention may be used, individually or in panels comprising a plurality of kidney injury markers, for risk stratification (that is, to identify sepsis patients at risk for a future injury to renal function, for future progression to reduced renal function, for future progression to ARF, for future improvement in renal function, etc.); for diagnosis of existing disease (that is, to identify sepsis patients who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a sepsis patient will require renal replacement therapy (i.e., hemodialysis, peritoneal dialysis, hemofiltration, and/or renal transplantation, a decreased or increased risk that a sepsis patient will recover from an injury to renal function, a decreased or increased risk that a sepsis patient will recover from ARF, a decreased or increased risk that a sepsis patient will progress to end stage renal disease, a decreased or increased risk that a sepsis patient will progress to chronic renal failure, a decreased or increased risk that a sepsis patient will suffer rejection of a transplanted kidney, etc.

In a first aspect, the present invention relates to methods for evaluating renal status in a sepsis patient. These methods comprise performing an assay method that is configured to detect one or more biomarkers selected from the group consisting of Insulin-like growth factor-binding protein 7, Beta-2-glycoprotein 1, Metalloproteinase inhibitor 2, Alpha-1 Antitrypsin, Leukocyte elastase, Serum Amyloid P Component, C-X-C motif chemokine 6, Immunoglobulin A, Immunoglobulin G subclass I, C-C motif chemokine 24, Neutrophil collagenase, Cathepsin D, C-X-C motif chemokine 13, Involucrin, Interleukin-6 receptor subunit beta, Hepatocyte Growth Factor, CXCL-1, -2, -3, Immunoglobulin G subclass II, Metalloproteinase inhibitor 4, C-C motif chemokine 18, Matrilysin, C-X-C motif chemokine 11, and Antileukoproteinase in a body fluid sample obtained from the sepsis patient. The assay result(s), for example measured concentration(s) of one or more biomarkers selected from the group consisting of Insulin-like growth factor-binding protein 7, Beta-2-glycoprotein 1, Metalloproteinase inhibitor 2, Alpha-1 Antitrypsin, Leukocyte elastase, Serum Amyloid P Component, C-X-C motif chemokine 6, Immunoglobulin A, Immunoglobulin G subclass I, C-C motif chemokine 24, Neutrophil collagenase, Cathepsin D, C-X-C motif chemokine 13, Involucrin, Interleukin-6 receptor subunit beta, Hepatocyte Growth Factor, CXCL-1, -2, -3, Immunoglobulin G subclass II, Metalloproteinase inhibitor 4, C-C motif chemokine 18, Matrilysin, C-X-C motif chemokine 11, and Antileukoproteinase is/are then correlated to the renal status of the sepsis patient. This correlation to renal status may include correlating the assay result(s) to one or more of risk stratification, diagnosis, prognosis, staging, classifying and monitoring of the sepsis patient as described herein. Thus, the present invention utilizes one or more kidney injury markers of the present invention for the evaluation of renal injury in a sepsis patient.

In certain embodiments, the methods for evaluating renal status described herein are methods for risk stratification of the sepsis patient; that is, assigning a likelihood of one or more future changes in renal status to the sepsis patient. In these embodiments, the assay result(s) is/are correlated to one or more such future changes. The following are preferred risk stratification embodiments.

In preferred risk stratification embodiments, these methods comprise determining a sepsis patient's risk for a future injury to renal function, and the assay result(s) is/are correlated to a likelihood of such a future injury to renal function. For example, the measured concentration(s) may each be compared to a threshold value. For a "positive going" kidney injury marker, an increased likelihood of suffering a future injury to renal function is assigned to the sepsis patient when the measured concentration is above the threshold, relative to a likelihood assigned when the measured concentration is below the threshold. For a "negative going" kidney injury marker, an increased likelihood of suffering a future injury to renal function is assigned to the sepsis patient when the measured concentration is below the threshold, relative to a likelihood assigned when the measured concentration is above the threshold.

In other preferred risk stratification embodiments, these methods comprise determining a sepsis patient's risk for future reduced renal function, and the assay result(s) is/are correlated to a likelihood of such reduced renal function. For example, the measured concentrations may each be compared to a threshold value. For a "positive going" kidney injury marker, an increased likelihood of suffering a future reduced renal function is assigned to the sepsis patient when the measured concentration is above the threshold, relative to a likelihood assigned when the measured concentration is below the threshold. For a "negative going" kidney injury marker, an increased likelihood of future reduced renal function is assigned to the sepsis patient when the measured concentration is below the threshold, relative to a likelihood assigned when the measured concentration is above the threshold.

In still other preferred risk stratification embodiments, these methods comprise determining a sepsis patient's likelihood for a future improvement in renal function, and the assay result(s) is/are correlated to a likelihood of such a future improvement in renal function. For example, the measured concentration(s) may each be compared to a threshold value. For a "positive going" kidney injury marker, an increased likelihood of a future improvement in renal function is assigned to the sepsis patient when the measured concentration is below the threshold, relative to a likelihood assigned when the measured concentration is above the threshold. For a "negative going" kidney injury marker, an increased likelihood of a future improvement in renal function is assigned to the sepsis patient when the measured concentration is above the threshold, relative to a likelihood assigned when the measured concentration is below the threshold.

In yet other preferred risk stratification embodiments, these methods comprise determining a sepsis patient's risk for progression to ARF, and the result(s) is/are correlated to a likelihood of such progression to ARF. For example, the measured concentration(s) may each be compared to a threshold value. For a "positive going" kidney injury marker, an increased likelihood of progression to ARF is assigned to the sepsis patient when the measured concentration is above the threshold, relative to a likelihood assigned when the measured concentration is below the threshold. For a "negative going" kidney injury marker, an increased likelihood of progression to ARF is assigned to the sepsis patient when the measured concentration is below the threshold, relative to a likelihood assigned when the measured concentration is above the threshold.

And in other preferred risk stratification embodiments, these methods comprise determining a sepsis patient's outcome risk, and the assay result(s) is/are correlated to a likelihood of the occurrence of a clinical outcome related to a renal injury suffered by the sepsis patient. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the sepsis patient when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the sepsis patient when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the sepsis patient. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the sepsis patient is equivalent to diagnosis of a current condition.

In other embodiments, the methods for evaluating renal status described herein are methods for diagnosing a renal injury in a sepsis patient; that is, assessing whether or not a sepsis patient has suffered from an injury to renal function, reduced renal function, or ARF. In these embodiments, the assay result(s), for example measured concentration(s) of one or more biomarkers selected from the group consisting of Insulin-like growth factor-binding protein 7, Beta-2-glycoprotein 1, Metalloproteinase inhibitor 2, Alpha-1 Antitrypsin, Leukocyte elastase, Serum Amyloid P Component, C-X-C motif chemokine 6, Immunoglobulin A, Immunoglobulin G subclass I, C-C motif chemokine 24, Neutrophil collagenase, Cathepsin D, C-X-C motif chemokine 13, Involucrin, Interleukin-6 receptor subunit beta, Hepatocyte Growth Factor, CXCL-1, -2, -3, Immunoglobulin G subclass II, Metalloproteinase inhibitor 4, C-C motif chemokine 18, Matrilysin, C-X-C motif chemokine 11, and Antileukoproteinase is/are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s) is/are correlated to the occurrence or nonoccurrence of such an injury. For example, each of the measured concentration(s) may be compared to a threshold value. For a positive going marker, an increased likelihood of the occurrence of an injury to renal function is assigned to the sepsis patient when the measured concentration is above the threshold (relative to the likelihood assigned when the measured concentration is below the threshold); alternatively, when the measured concentration is below the threshold, an increased likelihood of the nonoccurrence of an injury to renal function may be assigned to the sepsis patient (relative to the likelihood assigned when the measured concentration is above the threshold). For a negative going marker, an increased likelihood of the occurrence of an injury to renal function is assigned to the sepsis patient when the measured concentration is below the threshold (relative to the likelihood assigned when the measured concentration is above the threshold); alternatively, when the measured concentration is above the threshold, an increased likelihood of the nonoccurrence of an injury to renal function may be assigned to the sepsis patient (relative to the likelihood assigned when the measured concentration is below the threshold).

In other preferred diagnostic embodiments, these methods comprise diagnosing the occurrence or nonoccurrence of reduced renal function, and the assay result(s) is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the sepsis patient when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the sepsis patient (relative to the likelihood assigned when the measured concentration is above the threshold). For a negative going marker, an increased likelihood of the occurrence of an injury causing reduced renal function is assigned to the sepsis patient when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the sepsis patient (relative to the likelihood assigned when the measured concentration is below the threshold).

In yet other preferred diagnostic embodiments, these methods comprise diagnosing the occurrence or nonoccurrence of ARF, and the assay result(s) is/are correlated to the occurrence or nonoccurrence of an injury causing ARF. For example, each of the measured concentration(s) may be compared to a threshold value. For a positive going marker, an increased likelihood of the occurrence of ARF is assigned to the sepsis patient when the measured concentration is above the threshold (relative to the likelihood assigned when the measured concentration is below the threshold); alternatively, when the measured concentration is below the threshold, an increased likelihood of the nonoccurrence of ARF may be assigned to the sepsis patient (relative to the likelihood assigned when the measured concentration is above the threshold). For a negative going marker, an increased likelihood of the occurrence of ARF is assigned to the sepsis patient when the measured concentration is below the threshold (relative to the likelihood assigned when the measured concentration is above the threshold); alternatively, when the measured concentration is above the threshold, an increased likelihood of the nonoccurrence of ARF may be assigned to the sepsis patient (relative to the likelihood assigned when the measured concentration is below the threshold).

In still other preferred diagnostic embodiments, these methods comprise diagnosing a sepsis patient as being in need of renal replacement therapy, and the assay result(s) is/are correlated to a need for renal replacement therapy. For example, each of the measured concentration(s) may be compared to a threshold value. For a positive going marker, an increased likelihood of the occurrence of an injury creating a need for renal replacement therapy is assigned to the sepsis patient when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the sepsis patient (relative to the likelihood assigned when the measured concentration is above the threshold). For a negative going marker, an increased likelihood of the occurrence of an injury creating a need for renal replacement therapy is assigned to the sepsis patient when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the sepsis patient (relative to the likelihood assigned when the measured concentration is below the threshold).

In still other preferred diagnostic embodiments, these methods comprise diagnosing a sepsis patient as being in need of renal transplantation, and the assay result (s0 is/are correlated to a need for renal transplantation. For example, each of the measured concentration(s) may be compared to a threshold value. For a positive going marker, an increased likelihood of the occurrence of an injury creating a need for renal transplantation is assigned to the sepsis patient when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the sepsis patient (relative to the likelihood assigned when the measured concentration is above the threshold). For a negative going marker, an increased likelihood of the occurrence of an injury creating a need for renal transplantation is assigned to the sepsis patient when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the sepsis patient (relative to the likelihood assigned when the measured concentration is below the threshold).

In still other embodiments, the methods for evaluating renal status described herein are methods for monitoring a renal injury in a sepsis patient; that is, assessing whether or not renal function is improving or worsening in a sepsis patient who has suffered from an injury to renal function, reduced renal function, or ARF. In these embodiments, the assay result(s), for example measured concentration(s) of one or more biomarkers selected from the group consisting of Insulin-like growth factor-binding protein 7, Beta-2-glycoprotein 1, Metalloproteinase inhibitor 2, Alpha-1 Antitrypsin, Leukocyte elastase, Serum Amyloid P Component, C-X-C motif chemokine 6, Immunoglobulin A, Immunoglobulin G subclass I, C-C motif chemokine 24, Neutrophil collagenase, Cathepsin D, C-X-C motif chemokine 13, Involucrin, Interleukin-6 receptor subunit beta, Hepatocyte Growth Factor, CXCL-1, -2, -3, Immunoglobulin G subclass II, Metalloproteinase inhibitor 4, C-C motif chemokine 18, Matrilysin, C-X-C motif chemokine 11, and Antileukoproteinase is/are correlated to the occurrence or nonoccurrence of a change in renal status. The following are preferred monitoring embodiments.

In preferred monitoring embodiments, these methods comprise monitoring renal status in a sepsis patient suffering from an injury to renal function, and the assay result(s) is/are correlated to the occurrence or nonoccurrence of a change in renal status in the sepsis patient. For example, the measured concentration(s) may be compared to a threshold value. For a positive going marker, when the measured concentration is above the threshold, a worsening of renal function may be assigned to the sepsis patient; alternatively, when the measured concentration is below the threshold, an improvement of renal function may be assigned to the sepsis patient. For a negative going marker, when the measured concentration is below the threshold, a worsening of renal function may be assigned to the sepsis patient; alternatively, when the measured concentration is above the threshold, an improvement of renal function may be assigned to the sepsis patient.

In other preferred monitoring embodiments, these methods comprise monitoring renal status in a sepsis patient suffering from reduced renal function, and the assay result(s) is/are correlated to the occurrence or nonoccurrence of a change in renal status in the sepsis patient. For example, the measured concentration(s) may be compared to a threshold value. For a positive going marker, when the measured concentration is above the threshold, a worsening of renal function may be assigned to the sepsis patient; alternatively, when the measured concentration is below the threshold, an improvement of renal function may be assigned to the sepsis patient. For a negative going marker, when the measured concentration is below the threshold, a worsening of renal function may be assigned to the sepsis patient; alternatively, when the measured concentration is above the threshold, an improvement of renal function may be assigned to the sepsis patient.

In yet other preferred monitoring embodiments, these methods comprise monitoring renal status in a sepsis patient suffering from acute renal failure, and the assay result(s) is/are correlated to the occurrence or nonoccurrence of a change in renal status in the sepsis patient. For example, the measured concentration(s) may be compared to a threshold value. For a positive going marker, when the measured concentration is above the threshold, a worsening of renal function may be assigned to the sepsis patient; alternatively, when the measured concentration is below the threshold, an improvement of renal function may be assigned to the sepsis patient. For a negative going marker, when the measured concentration is below the threshold, a worsening of renal function may be assigned to the sepsis patient; alternatively, when the measured concentration is above the threshold, an improvement of renal function may be assigned to the sepsis patient.

In still other embodiments, the methods for evaluating renal status described herein are methods for classifying a renal injury in a sepsis patient; that is, determining whether a renal injury in a sepsis patient is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a sepsis patient will progress to a particular RIFLE stage. In these embodiments, the assay result(s), for example measured concentration(s) of one or more biomarkers selected from the group consisting of Insulin-like growth factor-binding protein 7, Beta-2-glycoprotein 1, Metalloproteinase inhibitor 2, Alpha-1 Antitrypsin, Leukocyte elastase, Serum Amyloid P Component, C-X-C motif chemokine 6, Immunoglobulin A, Immunoglobulin G subclass I, C-C motif chemokine 24, Neutrophil collagenase, Cathepsin D, C-X-C motif chemokine 13, Involucrin, Interleukin-6 receptor subunit beta, Hepatocyte Growth Factor, CXCL-1, -2, -3, Immunoglobulin G subclass II, Metalloproteinase inhibitor 4, C-C motif chemokine 18, Matrilysin, C-X-C motif chemokine 11, and Antileukoproteinase is/are correlated to a particular class and/or subclass. The following are preferred classification embodiments.

In preferred classification embodiments, these methods comprise determining whether a renal injury in a sepsis patient is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a sepsis patient will progress to a particular RIFLE stage, and the assay result(s) is/are correlated to the injury classification for the sepsis patient. For example, the measured concentration may be compared to a threshold value, and when the measured concentration is above the threshold, a particular classification is assigned; alternatively, when the measured concentration is below the threshold, a different classification may be assigned to the sepsis patient.

A variety of methods may be used by the skilled artisan to arrive at a desired threshold value for use in these methods. For example, the threshold value may be determined from a population of normal sepsis patients by selecting a concentration representing the $75^{th}$, $85^{th}$, $90^{th}$, $95^{th}$, or $99^{th}$ percentile of a kidney injury marker measured in such normal sepsis patients. Alternatively, the threshold value may be determined from a "diseased" population of sepsis patients, e.g., those suffering from an injury or having a predisposition for an injury (e.g., progression to ARF or some other clinical outcome such as death, dialysis, renal transplantation, etc.), by selecting a concentration representing the $75^{th}$, $85^{th}$, $90^{th}$, $95^{th}$, or $99^{th}$ percentile of a kidney injury marker measured in such sepsis patients. In another alternative, the threshold value may be determined from a prior measurement of a kidney injury marker in the same sepsis patient; that is, a temporal change in the level of a kidney injury marker in the sepsis patient may be used to assign risk to the sepsis patient.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the sepsis patient, the occurrence of an injury, a classification, etc. In yet another alternative, a threshold that can provide an acceptable level of specificity and sensitivity in separating a population of sepsis patients into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a sepsis patient. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to sepsis patients based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the sepsis patient selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for diagnosis, differential diagnosis, risk stratification, monitoring, classifying and determination of treatment regimens in sepsis patients diagnosed with sepsis. In various embodiments, a measured concentration of one or more biomarkers selected from the group consisting of Insulin-like growth factor-binding protein 7, Beta-2-glycoprotein 1, Metalloproteinase inhibitor 2, Alpha-1 Antitrypsin, Leukocyte elastase, Serum Amyloid P Component, C-X-C motif chemokine 6, Immunoglobulin A, Immunoglobulin G subclass I, C-C motif chemokine 24, Neutrophil collagenase, Cathepsin D, C-X-C motif chemokine 13, Involucrin, Interleukin-6 receptor subunit beta, Hepatocyte Growth Factor, CXCL-1, -2, -3, Immunoglobulin G subclass II, Metalloproteinase inhibitor 4, C-C motif chemokine 18, Matrilysin, C-X-C motif chemokine 11, and Antileukoproteinase or one or more markers related thereto, are correlated to the renal status of the sepsis patient.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in their entirety:

| Type | Risk Factors |
|---|---|
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |

| Type | Risk Factors |
|---|---|
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of sepsis patients with ARF may be as low as about 60%.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, Curr Opin Nephrol Hypertens 14:265-270, 2005 and Chertow et al, J Am Soc Nephrol 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., Crit Care. 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production<0.5 ml/kg/hr for 12 h;

"Failure": serum creatinine increased 3.0 fold from baseline OR creatinine >355 μmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, Crit. Care Med. 36: S141-45, 2008 and Ricci et al., Kidney Int. 73, 538-546, 2008, each hereby incorporated by reference in its entirety, the RIFLE criteria provide a uniform definition of AKI which has been validated in numerous studies.

More recently, Mehta et al., Crit. Care 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine≥354 µmol/L accompanied by an acute increase of at least 44 µmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (≥8.8 µmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (≥26.4 µmol/1), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

As used herein, the term "Insulin-like growth factor-binding protein 7" or "IGFBP7" refers to one or more polypeptides present in a biological sample that are derived from the Insulin-like growth factor-binding protein 7 precursor (human precursor: Swiss-Prot Q16270 (SEQ ID NO: 1))

```
            10         20         30         40
    MERPSLRALL LGAAGLLLLL LPLSSSSSSD TCGPCEPASC 50         60         70         80
    PPLPPLGCLL GETRDACGCC PMCARGEGEP CGGGGAGRGY 90        100        110        120
    CAPGMECVKS RKRRKGKAGA AAGGPGVSGV CVCKSRYPVC 130        140        150        160
    GSDGTTYPSG CQLRAASQRA ESRGEKAITQ VSKGTCEQGP 170        180        190        200
    SIVTPPKDIW NVTGAQVYLS CEVIGIPTPV LIWNKVKRGH 210        220        230        240
    YGVQRTELLP GDRDNLAIQT RGGPEKHEVT GWVLVSPLSK 250        260        270        280
    EDAGEYECHA SNSQGQASAS AKITVVDALH EIPVKKGEGA EL
```

The following domains have been identified in Insulin-like growth factor-binding protein 7:

| Residues | Length | Domain ID |
|---|---|---|
| 1-26 | 26 | Signal peptide |
| 27-282 | 256 | Insulin-like growth factor-binding protein 7 |

As used herein, the term "Beta-2-glycoprotein 1" refers to one or polypeptides present in a biological sample that are derived from the Beta-2-glycoprotein 1 precursor (human precursor: Swiss-Prot P02749 (SEQ ID NO: 2)).

```
            10         20         30         40
    MISPVLILFS SFLCHVAIAG RTCPKPDDLP FSTVVPLKTF 50         60         70         80
    YEPGEEITYS CKPGYVSRGG MRKFICPLTG LWPINTLKCT 90        100        110        120
    PRVCPFAGIL ENGAVRYTTF EYPNTISFSC NTGFYLNGAD 130        140        150        160
    SAKCTEEGKW SPELPVCAPI ICPPPSIPTF ATLRVYKPSA 170        180        190        200
    GNNSLYRDTA VFECLPQHAM FGNDTITCTT HGNWTKLPEC
```

-continued

```
           210        220        230        240
    REVKCPFPSR PDNGFVNYPA KPTLYYKDKA TFGCHDGYSL 250        260        270        280
    DGPEEIECTK LGNWSAMPSC KASCKVPVKK ATVVYQGERV 290        300        310        320
    KIQEKFKNGM LHGDKVSFFC KNKEKKCSYT EDAQCIDGTI 330        340
    EVPKCFKEHS SLAFWKTDAS DVKPC
```

The following domains have been identified in Beta-2-glycoprotein 1:

| Residues | Length | Domain ID |
|---|---|---|
| 1-19 | 19 | Signal sequence |
| 20-345 | 326 | Beta-2-glycoprotein 1 |

In addition, several naturally occurring variants have been identified:

| Residue | Change |
|---|---|
| 5 | V to A |
| 107 | S to N |
| 154 | R to H |
| 266 | V to L |
| 325 | C to G |
| 335 | W to S |

As used herein, the term "Metalloproteinase inhibitor 2" refers to one or more polypeptides present in a biological sample that are derived from the Metalloproteinase inhibitor 2 precursor (human precursor: Swiss-Prot P16035 (SEQ ID NO: 3)).

```
           10         20         30         40
    MGAAARTLRL ALGLLLLATL LRPADACSCS PVHPQQAFCN 50         60         70         80
    ADVVIRAKAV SEKEVDSGND IYGNPIKRIQ YEIKQIKMFK 90        100        110        120
    GPEKDIEFIY TAPSSAVCGV SLDVGGKKEY LIAGKAEGDG 130        140        150        160
    KMHITLCDFI VPWDTLSTTQ KKSLNHRYQM GCECKITRCP 170        180        190        200
    MIPCYISSPD ECLWMDWVTE KNINGHQAKF FACIKRSDGS 210        220
    CAWYRGAAPP KQEFLDIEDP
```

The following domains have been identified in Metalloproteinase inhibitor 2:

| Residues | Length | Domain ID |
|---|---|---|
| 1-26 | 26 | Signal peptide |
| 27-220 | 194 | Metalloproteinase inhibitor 2 |

As used herein, the term "alpha-1-antitrypsin" refers to one or more polypeptides present in a biological sample that are derived from the alpha-1-antitrypsin precursor (human precursor: Swiss-Prot P01009 (SEQ ID NO: 4)).

```
           10         20         30         40
    MPSSVSWGIL LLAGLCCLVP VSLAEDPQGD AAQKTDTSHH 50         60         70         80
    DQDHPTFNKI TPNLAEFAFS LYRQLAHQSN STNIFFSPVS 90        100        110        120
    IATAFAMLSL GTKADTHDEI LEGLNFNLTE IPEAQIHEGF 130        140        150        160
    QELLRTLNQP DSQLQLTTGN GLFLSEGLKL VDKFLEDVKK 170        180        190        200
    LYHSEAFTVN FGDTEEAKKQ INDYVEKGTQ GKIVDLVKEL 210        220        230        240
    DRDTVFALVN YIFFKGKWER PFEVKDTEEE DFHVDQVTTV 250        260        270        280
    KVPMMKRLGM FNIQHCKKLS SWVLLMKYLG NATAIFFLPD 290        300        310        320
    EGKLQHLENE LTHDIITKFL ENEDRRSASL HLPKLSITGT 330        340        350        360
    YDLKSVLGQL GITKVFSNGA DLSGVTEEAP LKLSKAVHKA 370        380        390        400
    VLTIDEKGTE AAGAMFLEAI PMSIPPEVKF NKPFVFLMIE

410
    QNTKSPLFMG KVVNPTQK
```

The following domains have been identified in alpha-1-antitrypsin:

| Residues | Length | Domain ID |
|---|---|---|
| 1-24 | 24 | signal sequence |
| 25-418 | 394 | alpha-1-antitrypsin |

As used herein, the term "leukocyte elastase" refers to one or more polypeptides present in a biological sample that are derived from the leukocyte elastase precursor (human precursor: Swiss-Prot P08246 (SEQ ID NO: 5)).

```
           10         20         30         40
    MTLGRRLACL FLACVLPALL LGGTALASEI VGGRRARPHA 50         60         70         80
    WPFMVSLQLR GGHFCGATLI APNFVMSAAH CVANVNVRAV 90        100        110        120
    RVVLGAHNLS RREPTRQVFA VQRIFENGYD PVNLLNDIVI 130        140        150        160
    LQLNGSATIN ANVQVAQLPA QGRRLGNGVQ CLAMGWGLLG 170        180        190        200
    RNRGIASVLQ ELNVTVVTSL CRRSNVCTLV RGRQAGVCFG 210        220        230        240
    DSGSPLVCNG LIHGIASFVR GGCASGLYPD AFAPVAQFVN 250        260
    WIDSIIQRSE DNPCPHPRDP DPASRTH
```

The following domains have been identified in leukocyte elastase:

| Residues | Length | Domain ID |
|---|---|---|
| 1-27 | 315 | signal sequence |
| 28-29 | 2 | pro-peptide |
| 30-267 | 238 | leukocyte elastase |

As used herein, the term "Serum amyloid P-component" refers to one or more polypeptides present in a biological sample that are derived from the Serum amyloid P-component precursor (human precursor: Swiss-Prot P02743 (SEQ ID NO: 6)).

```
         10         20         30         40
MNKPLLWISV LTSLLEAFAH TDLSGKVFVF PRESVTDHVN 50         60         70         80
LITPLEKPLQ NFTLCFRAYS DLSRAYSLFS YNTQGRDNEL 90        100        110        120
LVYKERVGEY SLYIGRHKVT SKVIEKFPAP VHICVSWESS 130        140        150        160
SGIAEFWING TPLVKKGLRQ GYFVEAQPKI VLGQEQDSYG 170        180        190        200
GKFDRSQSFV GEIGDLYMWD SVLPPENILS AYQGTPLPAN 210        220
ILDWQALNYE IRGYVIIKPL VWV
```

The following domains have been identified in Serum amyloid P-component:

| Residues | Length | Domain ID |
|---|---|---|
| 1-19 | 19 | Signal peptide |
| 20-223 | 204 | Serum amyloid P-component |
| 20-222 | 203 | Serum amyloid P-component (1-203) |

As used herein, the term "C-X-C motif chemokine 6" refers to one or more polypeptides present in a biological sample that are derived from the C-X-C motif chemokine 6 precursor (human precursor: Swiss-Prot P80162 (SEQ ID NO: 7))

```
         10         20         30         40         50         60
MSLPSSRAAR VPGPSGSLCA LLALLLLLTP PGPLASAGPV SAVLTELRCT CLRVTLRVNP 70         80         90        100        110
KTIGKLQVFP AGPQCSKVEV VASLKNGKQV CLDPEAPFLK KVIQKILDSG NKKN
```

The following domains have been identified in C-X-C motif chemokine 6:

| Residues | Length | Domain ID |
|---|---|---|
| 1-37 | 37 | Signal peptide |
| 38-114 | 77 | C—X—C motif chemokine 6 |
| 40-114 | 75 | C—X—C motif chemokine 6 (N-processed variant 1) |
| 43-114 | 72 | C—X—C motif chemokine 6 (N-processed variant 2) |
| 46-114 | 69 | C—X—C motif chemokine 6 (N-processed variant 3) |

As used herein, the term "C-C motif chemokine 24" refers to one or more polypeptides present in a biological sample that are derived from the C-C motif chemokine 24 precursor (human precursor: Swiss-Prot O00175 (SEQ ID NO: 8)).

```
         10         20         30         40
    MAGLMTIVTS LLFLGVCAHH IIPTGSVVIP SPCCMFFVSK 50         60         70         80
    RIPENRVVSY QLSSRSTCLK AGVIFTTKKG QQFCGDPKQE 90        100        110
    WVQRYMKNLD AKQKKASPRA RAVAVKGPVQ RYPGNQTTC
```

The following domains have been identified in C-C motif chemokine 24:

| Residues | Length | Domain ID |
|---|---|---|
| 1-26 | 26 | Signal peptide |
| 27-119 | 93 | C-C motif chemokine 24 |

As used herein, the term "Neutrophil collagenase" (also known as MMP-8 and matrix metalloproteinase 8) refers to one or more polypeptides present in a biological sample that are derived from the Neutrophil collagenase precursor (human precursor: Swiss-Prot P22894 (SEQ ID NO: 9)).

```
         10         20         30         40         50         60
    MFSLKTLPFL LLLHVQISKA FPVSSKEKNT KTVQDYLEKF YQLPSNQYQS TRKNGTNVIV 70         80         90        100        110        120
    EKLKEMQRFF GLNVTGKPNE ETLDMMKKPR CGVPDSGGFM LTPGNPKWER TNLTYRIRNY 130        140        150        160        170        180
    TPQLSEAEVE RAIKDAFELW SVASPLIFTR ISQGEADINI AFYQRDHGDN SPFDGPNGIL 190        200        210        220        230        240
    AHAFQPGQGI GGDAHFDAEE TWTNTSANYN LFLVAAHEFG HSLGLAHSSD PGALMYPNYA 250        260        270        280        290        300
    FRETSNYSLP QDDIDGIQAI YGLSSNPIQP TGPSTPKPCD PSLTFDAITT LRGEILFFKD 310        320        330        340        350        360
    RYFWRRHPQL QRVEMNFISL FWPSLPTGIQ AAYEDFDRDL IFLFKGNQYW ALSGYDILQG 370        380        390        400        410        420
    YPKDISNYGF PSSVQAIDAA VFYRSKTYFF VNDQFWRYDN QRQFMEPGYP KSISGAFPGI 430        440        450        460
    ESKVDAVFQQ EHFFHVFSGP RYYAFDLIAQ RVTRVARGNK WLNCRYG
```

The following domains have been identified in Neutrophil collagenase:

| Residues | Length | Domain ID |
|---|---|---|
| 1-20 | 20 | Signal peptide |
| 21-100 | 80 | Activation peptide |
| 101-467 | 367 | Neutrophil collagenase |

As used herein, the term "Cathepsin D" refers to one or more polypeptides present in a biological sample that are derived from the Cathepsin D precursor (human precursor: Swiss-Prot P07339 (SEQ ID NO: 10)).

```
         10         20         30         40         50         60
    MQPSSLLPLA LCLLAAPASA LVRIPLHKFT SIRRTMSEVG GSVEDLIAKG PVSKYSQAVP
```

```
            70         80         90        100        110        120
AVTEGPIPEV LKNYMDAQYY GEIGIGTPPQ CFTVVFDTGS SNLWVPSIHC KLLDIACWIH 130        140        150        160        170        180
HKYNSDKSST YVKNGTSFDI HYGSGSLSGY LSQDTVSVPC QSASSASALG GVKVERQVFG 190        200        210        220        230        240
EATKQPGITF IAAKFDGILG MAYPRISVNN VLPVFDNLMQ QKLVDQNIFS FYLSRDPDAQ 250        260        270        280        290        300
PGGELMLGGT DSKYYKGSLS YLNVTRKAYW QVHLDQVEVA SGLTLCKEGC EAIVDTGTSL 310        320        330        340        350        360
MVGPVDEVRE LQKAIGAVPL IQGEYMIPCE KVSTLPAITL KLGGKGYKLS PEDYTLKVSQ 370        380        390        400        410
AGKTLCLSGF MGMDIPPPSG PLWILGDVFI GRYYTVFDRD NNRVGFAEAA RL
```

The following domains have been identified in Capthesin D:

| Residues | Length | Domain ID |
|---|---|---|
| 1-18 | 18 | Signal peptide |
| 19-64 | 46 | Activation peptide |
| 65-412 | 348 | Cathepsin D |
| 65-161 | 348 | Cathepsin D light chain |
| 169-412 | 348 | Cathepsin D heavy chain |

As used herein, the term "C-X-C Motif chemokine 13" refers to one or more polypeptides present in a biological sample that are derived from the C-X-C Motif chemokine 13 precursor (human precursor: Swiss-Prot O43927 (SEQ ID NO: 11)).

```
            10         20         30         40         50         60
MKFISTSLLL MLLVSSLSPV QGVLEVYYTS LRCRCVQESS VFIPRRFIDR IQILPRGNGC 70         80         90        100
PRKEIIVWKK NKSIVCVDPQ AEWIQRMMEV LRKRSSSTLP VPVFKRKIP
```

The following domains have been identified in C-X-C Motif chemokine 13:

| Residues | Length | Domain ID |
|---|---|---|
| 1-22 | 22 | Signal peptide |
| 23-109 | 87 | C—X—C Motif chemokine 13 |

As used herein, the term "Involucrin" refers to one or more polypeptides present in a biological sample that are derived from the Involucrin precursor (human precursor: Swiss-Prot P07476 (human precursor: SEQ ID NO: 12)).

```
            10         20         30         40         50         60
MSQQHTLPVT LSPALSQELL KTVPPPVNTH QEQMKQPTP  LPPPCQKVPVE LPVEVPSKQE 70         80         90        100        110        120
EKHMTAVKGL PEQECEQQQK EPQEQELQQQ HWEQHEEYQK AENPEQQLKQ EKTQRDQQLN 130        140        150        160        170        180
KQLEEEKKLL DQQLDQELVK RDEQLGMKKE QLLELPEQQE GHLKHLEQQE GQLKHPEQQE 190        200        210        220        230        240
GQLELPEQQE GQLELPEQQE GQLELPEQQE GQLELPEQQE GQLELPEQQE GQLELPQQQE 250        260        270        280        290        300
GQLELSEQQE GQLELSEQQE GQLKHLEHQE GQLEVPEEQM GQLKYLEQQE GQLKHLDQQE
```

```
       310        320        330        340        350        360
KQPELPEQQM GQLKHLEQQE GQPKHLEQQE GQLEQLEEQE GQLKHLEQQE GQLEHLEHQE 370        380        390        400        410        420
GQLGLPEQQV LQLKQLEKQQ GQPKHLEEEE GQLKHLVQQE GQLKHLVQQE GQLEQQERQV 430        440        450        460        470        480
EHLEQQVGQL KHLEEQEGQL KHLEQQQGQL EVPEQQVGQP KNLEQEEKQL ELPEQQEGQV 490        500        510        520        530        540
KHLEKQEAQL ELPEQQVGQP KHLEQQEKHL EHPEQQDGQL KHLEQQEGQL KDLEQQKGQL 550        560        570        580
EQPVFAPAPG QVQDIQPALP TKGEVLLPVE HQQQKQEVQW PPKHK
```

As used herein, the term "Interleukin-6 receptor subunit beta" refers to one or more polypeptides present in a biological sample that are derived from the Interleukin-6 receptor subunit beta precursor (human precursor: Swiss-Prot P40189 (SEQ ID NO: 13))

```
        10         20         30         40         50         60
MLTLQTWLVQ ALFIFLTTES TGELLDPCGY ISPESPVVQL HSNFTAVCVL KEKCMDYFHV 70         80         90        100        110        120
NANYIVWKTN HFTIPKEQYT IINRTASSVT FTDIASLNIQ LTCNILTFGQ LEQNVYGITI 130        140        150        160        170        180
ISGLPPEKPK NLSCIVNEGK KMRCEWDGGR ETHLETNFTL KSEWATHKFA DCKAKRDTPT 190        200        210        220        230        240
SCTVDYSTVY FVNIEVWVEA ENALGKVTSD HINFDPVYKV KPNPPHNLSV INSEELSSIL 250        260        270        280        290        300
KLTWTNPSIK SVIILKYNIQ YRTKDASTWS QIPPEDTAST RSSFTVQDLK PFTEYVFRIR 310        320        330        340        350        360
CMKEDGKGYW SDWSEEASGI TYEDRPSKAP SFWYKIDPSH TQGYRTVQLV WKTLPPFEAN 370        380        390        400        410        420
GKILDYEVTL TRWKSHLQNY TVNATKLTVN LTNDRYLATL TVRNLVGKSD AAVLTIPACD 430        440        450        460        470        480
FQATHPVMDL KAFPKDNMLW VEWTTPRESV KKYILEWCVL SDKAPCITDW QQEDGTVHRT 490        500        510        520        530        540
YLRGNLAESK CYLITVTPVY ADGPGSPESI KAYLKQAPPS KGPTVRTKKV GKNEAVLEWD 550        560        570        580        590        600
QLPVDVQNGF IRNYTIFYRT IIGNETAVNV DSSHTEYTLS SLTSDTLYMV RMAAYTDEGG 610        620        630        640        650        660
KDGPEFTFTT PKFAQGEIEA IVVPVCLAFL LTTLLGVLFC FNKRDLIKKH IWPNVPDPSK 670        680        690        700        710        720
SHIAQWSPHT PPRHNFNSKD QMYSDGNFTD VSVVEIEAND KKPFPEDLKS LDLFKKEKIN 730        740        750        760        770        780
TEGHSSGIGG SSCMSSSRPS ISSSDENESS QNTSSTVQYS TVVHSGYRHQ VPSVQVFSRS 790        800        810        820        830        840
ESTQPLLDSE ERPEDLQLVD HVDGGDGILP RQQYFKQNCS QHESSPDISH FERSKQVSSV 850        860        870        880        890        900
NEEDFVRLKQ QISDHISQSC GSGQMKMFQE VSAADAFGPG TEGQVERFET VGMEAATDEG

910
MPKSYLPQTV RQGGYMPQ
```

Most preferably, the Interleukin-6 receptor subunit beta assay detects one or more soluble forms of Interleukin-6 receptor subunit beta. Interleukin-6 receptor subunit beta is a type I membrane protein having a large extracellular domain, most or all of which is present in soluble forms of Interleukin-6 receptor subunit beta generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Interleukin-6 receptor subunit beta:

| Residues | Length | Domain ID |
|---|---|---|
| 1-22 | 22 | Signal peptide |
| 23-918 | 896 | Interleukin-6 receptor subunit beta |
| 642-918 | 277 | Cytoplasmic domain |
| 620-641 | 21 | transmembrane domain |
| 23-619 | 597 | Extracellular domain |
| 330-918 | 589 | Missing in isoform 2 |
| 325-329 | 5 | RPSKA (SEQ ID NO: 14) → NIASF (SEQ ID NO: 15) in isoform 2 |

As used herein, the term "Hepatocyte growth factor" refers to one or more polypeptides present in a biological sample that are derived from the Hepatocyte growth factor precursor (human precursor: Swiss-Prot P14210 (SEQ ID NO: 16)).

```
         10         20         30         40         50         60
  MWVTKLLPAL LLQHVLLHLL LLPIAIPYAE GQRKRRNTIH EFKKSAKTTL IKIDPALKIK 70         80         90        100        110        120
  TKKVNTADQC ANRCTRNKGL PFTCKAFVFD KARKQCLWFP FNSMSSGVKK EFGHEFDLYE 130        140        150        160        170        180
  NKDYIRNCII GKGRSYKGTV SITKSGIKCQ PWSSMIPHEH SFLPSSYRGK DLQENYCRNP 190        200        210        220        230        240
  RGEEGGPWCF TSNPEVRYEV CDIPQCSEVE CMTCNGESYR GLMDHTESGK ICQRWDHQTP 250        260        270        280        290        300
  HRHKFLPERY PDKGFDDNYC RNPDGQPRPW CYTLDPHTRW EYCAIKTCAD NTMNDTDVPL 310        320        330        340        350        360
  ETTECIQGQG EGYRGTVNTI WNGIPCQRWD SQYPHEHDMT PENFKCKDLR ENYCRNPDGS 370        380        390        400        410        420
  ESPWCFTTDP NIRVGYCSQI PNCDMSHGQD CYRGNGKNYM GNLSQTRSGL TCSMWDKNME 430        440        450        460        470        480
  DLHRHIFWEP DASKLNENYC RNPDDDAHGP WCYTGNPLIP WDYCPISRCE GDTTPTIVNL 490        500        510        520        530        540
  DHPVISCAKT KQLRVVNGIP TRTNIGWMVS LRYRNKHICG GSLIKESWVL TARQCFPSRD 550        560        570        580        590        600
  LKDYEAWLGI HDVHGRGDEK CKQVLNVSQL VYGPEGSDLV LMKLARPAVL DDFVSTIDLP 610        620        630        640        650        660
  NYGCTIPEKT SCSVYGWGYT GLINYDGLLR VAHLYIMGNE KCSQHHRGKV TLNESEICAG 670        680        690        700        710        720
  AEKIGSGPCE GDYGGPLVCE QHKMRMVLGV IVPGRGCAIP NRPGIFVRVA YYAKWIHKII

LTYKVPQS
```

The following domains have been identified in Hepatocyte growth factor:

| Residues | Length | Domain ID |
|---|---|---|
| 1-31 | 31 | signal sequence |
| 32-494 | 463 | Hepatocyte growth factor alpha chain |
| 495-728 | 234 | Hepatocyte growth factor beta chain |

As used herein, the term "Metalloproteinase inhibitor 4" refers to one or polypeptides present in a biological sample that are derived from the Metalloproteinase inhibitor 4 precursor (human precursor: Swiss-Prot Q99727 (SEQ ID NO: 17)).

```
        10         20         30         40         50         60
MPGSPRPAPS WVLLLRLLAL LRPPGLGEAC SCAPAHPQQH ICHSALVIRA KISSEKVVPA 70         80         90        100        110        120
SADPADTEKM LRYEIKQIKM FKGFEKVKDV QYIYTPFDSS LCGVKLEANS QKQYLLTGQV 130        140        150        160        170        180
LSDGKVFIHL CNYIEPWEDL SLVQRESLNH HYHLNCGCQI TTCYTVPCTI SAPNECLWTD 190        200        210        220
WLLERKLYGY QAQHYVCMKH VDGTCSWYRG HLPLRKEFVD IVQP
```

The following domains have been identified in Metalloproteinase inhibitor 4:

| Residues | Length | Domain ID |
|---|---|---|
| 1-27 | 27 | Signal sequence |
| 28-224 | 197 | Metalloproteinase inhibitor 4 |

As used herein, the term "C-C motif chemokine 18" refers to one or more polypeptides present in a biological sample that are derived from the C-C motif chemokine 18 precursor (human precursor: Swiss-Prot P55774 (SEQ ID NO: 18)).

```
        10         20         30         40         50         60
MKGLAAALLV LVCTMALCSC AQVGTNKELC CLVYTSWQIP QKFIVDYSET SPQCPKPGVI 70         80
LLTKRGRQIC ADPNKKWVQK YISDLKLNA
```

The following domains have been identified in C-C motif chemokine 18:

| Residues | Length | Domain ID |
|---|---|---|
| 1-20 | 20 | Signal peptide |
| 21-89 | 69 | C-C motif chemokine 18 |
| 21-88 | 68 | CCL 18 (1-68) |
| 23-89 | 67 | CCL 18 (3-69) |
| 24-89 | 66 | CCL 18 (4-69) |

As used herein, the term "Matrilysin" refers to one or more polypeptides present in a biological sample that are derived from the Matrilysin precursor (Swiss-Prot P09237 (human precursor: SEQ ID NO: 19))

```
        10         20         30         40         50         60
MRLTVLCAVC LLPGSLALPL PQEAGGMSEL QWEQAQDYLK RFYLYDSETK NANSLEAKLK 70         80         90        100        110        120
EMQKFFGLPI TGMLNSRVIE IMQKPRCGVP DVAEYSLFPN SPKWTSKVVT YRIVSYTRDL
```

```
           130        140        150        160        170        180
PHITVDRLVS KALNMWGKEI PLHFRKVVWG TADIMIGFAR GAHGDSYPFD GPGNTLAHAF 190        200        210        220        230        240
APGTGLGGDA HFDEDERWTD GSSLGINFLY AATHELGHSL GMGHSSDPNA VMYPTYGNGD 250        260
PQNFKLSQDD IKGIQKLYGK RSNSRKK
```

The following domains have been identified in Matrilysin:

| Residues | Length | Domain ID |
|---|---|---|
| 1-17 | 17 | signal peptide |
| 18-94 | 77 | activation peptide |
| 95-267 | 173 | Matrilysin |

As used herein, the term "C-X-C motif chemokine 11" refers to one or more polypeptides present in a biological sample that are derived from the C-X-C motif chemokine 11 precursor (human precursor: Swiss-Prot O14625 (SEQ ID NO: 20))

```
           10         20         30         40         50         60
MSVKGMAIAL AVILCATVVQ GFPMFKRGRC LCIGPGVKAV KVADIEKASI MYPSNNCDKI 70         80         90
EVIITLKENK GQRCLNPKSK QARLIIKKVE RKNF
```

The following domains have been identified in C-X-C motif chemokine 11:

| Residues | Length | Domain ID |
|---|---|---|
| 1-21 | 21 | signal peptide |
| 22-94 | 73 | C—X—C motif chemokine 11 |

As used herein, the term "C-X-C motif chemokines-1, -2, and -3" refers to one or more polypeptides present in a biological sample that are common to the C-X-C motif chemokines-1, -2, and -3 precursors (Swiss-Prot accession numbers of the human precursors: C-X-C motif chemokine-1 (P09341), -2 (P19875), and -3 (P19876)).

CXC motif chemokine-1 is also known as "Growth-regulated alpha protein" (human precursor Swiss-Prot P09341 (SEQ ID NO: 21)).

```
           10         20         30         40         50         60
MARAALSAAP SNPRLLRVAL LLLLLVAAGR RAAGASVATE LRCQCLQTLQ GIHPKNIQSV 70         80         90        100
NVKSPGPHCA QTEVIATLKN GRKACLNPAS PIVKKIIEKM LNSDKSN
```

The following domains have been identified in Growth-regulated alpha protein:

| Residues | Length | Domain ID |
|---|---|---|
| 1-34 | 34 | Signal peptide |
| 35-107 | 73 | Growth-regulated alpha protein |
| 38-107 | 70 | GRO-alpha (4-73) |
| 39-107 | 69 | GRO-alpha (5-73) |
| 40-107 | 68 | GRO-alpha (6-73) |

CXC motif chemokine-2 is also known as "Macrophage inflammatory protein 2-alpha" (human precursor Swiss-Prot P19875 (SEQ ID NO: 22)).

```
         10         20         30         40         50         60
MARATLSAAP SNPRLLRVAL LLLLLVAASR RAAGAPLATE LRCQCLQTLQ GIHLKNIQSV 70         80         90        100
KVKSPGPHCA QTEVIATLKN GQKACLNPAS PMVKKIIEKM LKNGKSN
```

The following domains have been identified in Macrophage inflammatory protein 2-alpha:

| Residues | Length | Domain ID |
|---|---|---|
| 1-34 | 34 | Signal peptide |
| 35-107 | 73 | C—X—C motif chemokine 2 |
| 39-107 | 69 | GRO-beta (5-73) |

CXC motif chemokine-2 is also known as "Growth-regulated protein gamma" (human precursor Swiss-Prot P19876 (SEQ ID NO: 23)).

```
         10         20         30         40         50         60
MAHATLSAAP SNPRLLRVAL LLLLLVAASR RAAGASVVTE LRCQCLQTLQ GIHLKNIQSV 70         80         90        100
NVRSPGPHCA QTEVIATLKN GKKACLNPAS PMVQKIIEKI LNKGSTN
```

The following domains have been identified in C-X-C motif chemokine 3:

| Residues | Length | Domain ID |
|---|---|---|
| 1-34 | 34 | Signal peptide |
| 35-107 | 73 | C—X—C motif chemokine 3 |
| 39-107 | 73 | GRO-gamma (5-73) |

As used herein, the term "Antileukoproteinase" refers to one or more polypeptides present in a biological sample that are derived from the Antileukoproteinase precursor (Swiss-Prot P03973 (SEQ ID NO: 24)).

```
         10         20         30         40         50         60
MKSSGLFPFL VLLALGTLAP WAVEGSGKSF KAGVCPPKKS AQCLRYKKPE CQSDWQCPGK 70         80         90        100        110        120
KRCCPDTCGI KCLDPVDTPN PTRRKPGKCP VTYGQCLMLN PPNFCEMDGQ CKRDLKCCMG

130
MCGKSCVSPV KA
```

The following domains have been identified in Antileukoproteinase:

| Residues | Length | Domain ID |
|---|---|---|
| 1-25 | 25 | signal sequence |
| 26-132 | 107 | Antileukoproteinase |

As used herein, the term "IgA" refers to an antibody having two subclasses (IgA1 and IgA2) and which can exist in a dimeric form linked by a J chain (called secretory IgA, or sIgA). In its secretory form, IgA is the main immunoglobulin found in mucous secretions, including tears, saliva, colostrum and secretions from the genito-urinary tract, gastrointestinal tractprostate and respiratory epithelium. It is also found in small amounts in blood. IgA may be measured separately from other immunoglobulins such as IgG or IgM, for example, using antibodies which bind to the IgA α-chain.

As used herein, the terms "IgG1" and "IgG subclass I" refer to subclass 1 of the glycoprotein immunoglobulin G (IgG), a major effector molecule of the humoral immune response in man. Antibodies of the IgG class express their predominant activity during a secondary antibody response. The basic immunoglobulin G molecule has a four-chain structure, comprising two identical heavy (H) chains and two identical light (L) chains, linked together by inter-chain disulfide bonds. Each heavy chain is encoded by 4 distinct types of gene segments, designated $V_H$ (variable), D (diversity), $J_H$ (joining) and $C_H$ (constant). The variable region of the heavy chain is encoded by the $V_H$, D and $J_H$ segments. The light chains are encoded by the 3 gene segments, $V_L$, $J_L$ and $C_L$. The variable region of the light chains is encoded by the $V_L$ and $J_L$ segments.

As used herein, the terms "IgG2" and "IgG subclass II" refer to subclass 2 of the glycoprotein immunoglobulin G (IgG), a major effector molecule of the humoral immune response in man. Antibodies of the IgG class express their predominant activity during a secondary antibody response. The basic immunoglobulin G molecule has a four-chain structure, comprising two identical heavy (H) chains and two identical light (L) chains, linked together by inter-chain disulfide bonds. Each heavy chain is encoded by 4 distinct types of gene segments, designated $V_H$ (variable), D (diversity), $J_H$ (joining) and $C_H$ (constant). The variable region of the heavy chain is encoded by the $V_H$, D and $J_H$ segments. The light chains are encoded by the 3 gene segments, $V_L$, $J_L$ and $C_L$. The variable region of the light chains is encoded by the $V_L$ and $J_L$ segments.

The length and flexibility of the hinge region varies among the IgG subclasses. The hinge region of IgG1 encompasses amino acids 216-231 and since it is freely flexible, the Fab fragments can rotate about their axes of symmetry and move within a sphere centered at the first of two inter-heavy chain disulfide bridges (23). IgG2 has a shorter hinge than IgG1, with 12 amino acid residues and four disulfide bridges. The hinge region of IgG2 lacks a glycine residue, it is relatively short and contains a rigid poly-proline double helix, stabilised by extra inter-heavy chain disulfide bridges. These properties restrict the flexibility of the IgG2 molecule (24). IgG3 differs from the other subclasses by its unique extended hinge region (about four times as long as the IgG1 hinge), containing 62 amino acids (including 21 prolines and 11 cysteines), forming an inflexible poly-proline double helix (25,26). In IgG3 the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2.

The four IgG subclasses also differ with respect to the number of inter-heavy chain disulfide bonds in the hinge region (26). The structural differences between the IgG subclasses are also reflected in their susceptibility to proteolytic enzymes. IgG3 is very susceptible to cleavage by these enzymes, whereas IgG2 is relatively resistant. IgG1 and IgG4 exhibit an intermediary sensitivity, depending upon the enzyme used. Since these proteolytic enzymes all cleave IgG molecules near or within the hinge region, it is likely that the high sensitivity of IgG3 to enzyme digestion is related to its accessible hinge. Another structural difference between the human IgG subclasses is the linkage of the heavy and light chain by a disulfide bond. This bond links the carboxy-terminal of the light chain with the cysteine residue at position 220 (in IgG) or at position 131 (in IgG2, IgG3 and IgG4) of the CH1 sequence of the heavy chain.

As a consequence of the structural differences, the four IgG subclasses may be distinguished from one another, for example using antibodies that are specific for differences between the isoforms. In the present application, a level of IgG1 is determined using an assay which distinguishes this subclass, relative to the other subclasses.

As used herein, the term "relating a signal to the presence or amount" of an analyte reflects the following understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

The term "positive going" marker as that term is used herein refer to a marker that is determined to be elevated in sepsis patients suffering from a disease or condition, relative to sepsis patients not suffering from that disease or condition. The term "negative going" marker as that term is used herein refer to a marker that is determined to be reduced in sepsis patients suffering from a disease or condition, relative to sepsis patients not suffering from that disease or condition.

The term "sepsis patient" as used herein refers to a human or non-human organism. Thus, the methods and compositions described herein are applicable to both human and veterinary disease. Further, while a sepsis patient is preferably a living organism, the invention described herein may be used in post-mortem analysis as well. Preferred sepsis patients are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a sepsis patient, or may be obtained from biological materials intended to be provided to the sepsis patient. For example, a sample may be obtained from a kidney being evaluated for possible transplantation into a sepsis patient, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a sepsis patient of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the sepsis patient from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the sepsis patient relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and *The Immunoassay Handbook*, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGel™ resins (Rapp Polymere GmbH), AgroGel™ resins (I.L.S.A. Industria Lavorazione Sottoprodotti Animali S.P.A.), polyethylene glycol and acrylamide (PEGA) gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: r/c=K(n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Reciever Operating Characteristic ("ROC") arose from the field of signal dectection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1−specificity, the ROC graph is sometimes called the sensitivity vs (1−specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a sepsis patient belongs to one classification out of a plurality of classifications. Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr\text{-corrected}} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1: Septic Sepsis Patient Sample Collection

The objective of this study was to collect samples from patients expected to be in the ICU for at least 48 hours were enrolled. To be enrolled in the study, each patient must meet all of the following inclusion criteria and none of the following exclusion criteria:
Inclusion Criteria: males and females 18 years of age or older and which either acquire sepsis or have sepsis on admission.
Exclusion Criteria
known pregnancy;
institutionalized individuals;
previous renal transplantation;
known acutely worsening renal function prior to enrollment (e.g., any category of RIFLE criteria);
received dialysis (either acute or chronic) within 5 days prior to enrollment or in imminent need of dialysis at the time of enrollment;
known infection with human immunodeficiency virus (HIV) or a hepatitis virus;
meets only the SBP<90 mmHg inclusion criterion set forth above, and does not have shock in the attending physician's or principal investigator's opinion.

After providing informed consent, an EDTA anti-coagulated blood sample (10 mL) and a urine sample (25-30 mL) are collected from each patient. Blood and urine samples are then collected at 4 (±0.5) and 8 (±1) hours after contrast administration (if applicable); at 12 (±1), 24 (±2), and 48 (±2) hours after enrollment, and thereafter daily up to day 7 to day 14 while the sepsis patient is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 2: Immunoassay Format

Analytes are measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards.

Concentrations for the various markers are reported as follows:

| | |
|---|---|
| Insulin-like growth factor-binding protein 7 | ng/ml |
| Beta-2-glycoprotein 1 | ng/ml |
| Metalloproteinase inhibitor 2 | pg/ml |
| Alpha-1 Antitrypsin | ng/ml |
| Neutrophil Elastase | ng/ml |
| Serum Amyloid P Component | ng/ml |
| C—X—C motif chemokine 6 | pg/ml |
| Immunoglobulin A | ng/ml |
| Immunoglobulin G, subclass I | ng/ml |
| C-C motif chemokine 24 | pg/ml |
| Neutrophil collagenase | pg/ml |
| Cathepsin D | pg/ml |
| C—X—C motif chemokine 13 | pg/ml |
| Involucrin | ng/ml |
| Interleukin-6 receptor subunit beta | pg/ml |
| Hepatocyte Growth Factor | pg/ml |
| CXCL-1, -2, -3 mix | pg/ml |
| Immunoglobulin G, subclass II | ng/ml |
| Metalloproteinase inhibitor 4 | pg/ml |
| C-C motif chemokine 18 | ng/ml |
| Matrilysin | pg/ml |
| C—X—C motif chemokine 11 | pg/ml |
| Antileukoproteinase (WAP4) | pg/ml |

Example 3: Use of Kidney Injury Markers for Evaluating Sepsis Patients

Patients from the sepsis study (Example 1) were classified by kidney status as non-injury (0), risk of injury (R), injury (I), and failure (F) according to the maximum stage reached within 7 days of enrollment as determined by the RIFLE criteria. EDTA anti-coagulated blood samples (10 mL) and a urine samples (25-30 mL) were collected from each patient at enrollment, 4 (±0.5) and 8 (±1) hours after contrast administration (if applicable); at 12 (±1), 24 (±2), and 48 (±2) hours after enrollment, and thereafter daily up to day 7 to day 14 while the sepsis patient is hospitalized. Markers were each measured by standard immunoassay methods using commercially available assay reagents in the urine samples and the plasma component of the blood samples collected.

Two cohorts were defined to represent a "diseased" and a "normal" population. While these terms are used for convenience, "diseased" and "normal" simply represent two cohorts for comparison (say RIFLE 0 vs RIFLE R, I and F; RIFLE 0 vs RIFLE R; RIFLE 0 and R vs RIFLE I and F; etc.). The time "prior max stage" represents the time at which a sample is collected, relative to the time a particular patient reaches the lowest disease stage as defined for that cohort, binned into three groups which are +/−12 hours. For example, "24 hr prior" which uses 0 vs R, I, F as the two cohorts would mean 24 hr (+/−12 hours) prior to reaching stage R (or I if no sample at R, or F if no sample at R or I).

A receiver operating characteristic (ROC) curve was generated for each biomarker measured and the area under each ROC curve (AUC) is determined Patients in Cohort 2 were also separated according to the reason for adjudication to cohort 2 as being based on serum creatinine measurements (sCr), being based on urine output (UO), or being based on either serum creatinine measurements or urine output. Using the same example discussed above (0 vs R, I, F), for those patients adjudicated to stage R, I, or F on the basis of serum creatinine measurements alone, the stage 0 cohort may include patients adjudicated to stage R, I, or F on the basis of urine output; for those patients adjudicated to stage R, I, or F on the basis of urine output alone, the stage 0 cohort may include patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, in the data for patients adjudicated on the basis of serum creatinine measurements or urine output, the adjudication method which yielded the most severe RIFLE stage is used.

The ability to distinguish cohort 1 from Cohort 2 was determined using ROC analysis. SE is the standard error of the AUC, n is the number of sample or individual patients ("pts," as indicated). Standard errors are calculated as described in Hanley, J. A., and McNeil, B. J., The meaning and use of the area under a receiver operating characteristic (ROC) curve. Radiology (1982) 143: 29-36; p values are calculated with a two-tailed Z-test. An AUC<0.5 is indicative of a negative going marker for the comparison, and an AUC>0.5 is indicative of a positive going marker for the comparison.

Various threshold (or "cutoff") concentrations were selected, and the associated sensitivity and specificity for distinguishing cohort 1 from cohort 2 are determined OR is the odds ratio calculated for the particular cutoff concentration, and 95% CI is the confidence interval for the odds ratio.

In the following tables 1-12, a population which either acquire sepsis days 1-7 or have sepsis on admission are used as the disease cohort; in tables 13-24, only those patients with sepsis on admission were included.

Lengthy table referenced here

US10935548-20210302-T00001

Please refer to the end of the specification for access instructions.

Lengthy table referenced here

US10935548-20210302-T00002

Please refer to the end of the specification for access instructions.

Lengthy table referenced here

US10935548-20210302-T00003

Please refer to the end of the specification for access instructions.

Lengthy table referenced here

US10935548-20210302-T00004

Please refer to the end of the specification for access instructions.

Lengthy table referenced here

US10935548-20210302-T00005

Please refer to the end of the specification for access instructions.

Lengthy table referenced here

US10935548-20210302-T00006

Please refer to the end of the specification for access instructions.

Lengthy table referenced here

US10935548-20210302-T00007

Please refer to the end of the specification for access instructions.

Lengthy table referenced here

US10935548-20210302-T00008

Please refer to the end of the specification for access instructions.

Lengthy table referenced here

US10935548-20210302-T00009

Please refer to the end of the specification for access instructions.

Lengthy table referenced here

US10935548-20210302-T00010

Please refer to the end of the specification for access instructions.

Lengthy table referenced here

US10935548-20210302-T00011

Please refer to the end of the specification for access instructions.

Lengthy table referenced here

US10935548-20210302-T00012

Please refer to the end of the specification for access instructions.

Lengthy table referenced here

US10935548-20210302-T00013

Please refer to the end of the specification for access instructions.

Lengthy table referenced here

US10935548-20210302-T00014

Please refer to the end of the specification for access instructions.

Lengthy table referenced here

US10935548-20210302-T00015

Please refer to the end of the specification for access instructions.

Lengthy table referenced here

US10935548-20210302-T00016

Please refer to the end of the specification for access instructions.

Lengthy table referenced here

US10935548-20210302-T00017

Please refer to the end of the specification for access instructions.

Lengthy table referenced here

US10935548-20210302-T00018

Please refer to the end of the specification for access instructions.

Lengthy table referenced here

US10935548-20210302-T00019

Please refer to the end of the specification for access instructions.

Lengthy table referenced here

US10935548-20210302-T00020

Please refer to the end of the specification for access instructions.

Lengthy table referenced here

US10935548-20210302-T00021

Please refer to the end of the specification for access instructions.

Lengthy table referenced here

US10935548-20210302-T00022

Please refer to the end of the specification for access instructions.

Lengthy table referenced here

US10935548-20210302-T00023

Please refer to the end of the specification for access instructions.

Lengthy table referenced here

US10935548-20210302-T00024

Please refer to the end of the specification for access instructions.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

LENGTHY TABLES

The patent contains a lengthy table section. A copy of the table is available in electronic form from the USPTO web site (https://seqdata.uspto.gov/?pageRequest=docDetail&DocID=US10935548B2). An electronic copy of the table will also be available from the USPTO upon request and payment of the fee set forth in 37 CFR 1.19(b)(3).

---

We claim:

1. A method for treating acute kidney injury comprising:
(a) obtaining a urine sample from a subject determined to have sepsis;
(b) performing a first assay to measure a level or concentration of insulin-like growth factor-binding protein 7 in the urine sample and performing a second assay to measure a level or concentration of metalloproteinase inhibitor 2 in the urine sample;
(c) calculating a composite value comprising the level or concentration of insulin-like growth factor-binding protein 7 and the level or concentration of metalloproteinase inhibitor 2;
(d) comparing the composite value of (c) to a first predetermined threshold, wherein the first predetermined threshold comprises a predetermined level or concentration of urinary insulin-like growth factor-binding protein 7 and a predetermined level or concentration of urinary metalloproteinase inhibitor 2;
(e) identifying a subject at risk for occurrence of RIFLE I or F within 24 hours of the time at which the urine sample is obtained from the subject when the composite value is higher as compared to the first predetermined threshold; and
(f) treating the identified subject of (e), wherein the treating comprises initiating kidney replacement therapy, withdrawing delivery of compounds known to be damaging to the kidney, kidney transplant, or modifying diuretic administration, wherein the insulin-like growth factor-binding protein 7 comprises amino acid residues 27-282 of SEQ ID NO: 1.

2. The method of claim 1, wherein the level or concentration of urinary insulin-like growth factor-binding protein 7 obtained from the first assay is elevated as compared to a second predetermined threshold, wherein the second predetermined threshold comprises the predetermined level or concentration of urinary insulin-like growth factor-binding protein 7.

3. The method of claim 1, wherein the level or concentration of urinary metalloproteinase inhibitor 2 obtained from the second assay is elevated as compared to a third predetermined threshold, wherein the third predetermined threshold comprises the predetermined level or concentration of urinary metalloproteinase inhibitor 2.

4. The method of claim 1, comprising measuring the concentration of the insulin-like growth factor-binding protein 7 and the metalloproteinase inhibitor 2 in the sample.

5. The method of claim 1, wherein the sepsis is severe sepsis or septic shock.

6. The method of claim 1, wherein performing a first assay comprises contacting all or a portion of the urine sample with a first binding reagent which specifically binds to the insulin-like growth factor-binding protein 7, and generating a first assay result indicative of the level or concentration of the insulin-like growth factor-binding protein 7, and wherein performing a second assay comprises contacting all or a portion of the urine sample with a second binding reagent which specifically binds to metalloproteinase inhibitor 2, and generating a second assay result indicative of the level or concentration of the metalloproteinase inhibitor 2 to the second binding reagent.

7. The method of claim 1, wherein the composite value is obtained using a function that combines the level or concentration of insulin-like growth factor-binding protein 7 and the level or concentration of metalloproteinase inhibitor 2 into a single composite value.

8. The method of claim 1, wherein risk for occurrence of RIFLE I or F acute kidney injury is within 12 hours of the time at which urine sample is obtained.

9. The method of claim 1, wherein the subject is identified at risk for occurrence of RIFLE I within 24 hours of the time at which the urine sample is obtained from the subject.

10. The method of claim 1, wherein the subject is identified at risk for occurrence of RIFLE F within 24 hours of the time at which the urine sample is obtained from the subject.

11. The method of claim 1, wherein the subject has suffered from an injury to kidney function, reduced kidney function, or acute kidney failure.

12. The method of claim 1, wherein the subject is in RIFLE stage R.

13. A method for treating acute kidney injury comprising:
(a) obtaining a urine sample from a subject determined to have sepsis;
(b) measuring a level or concentration of insulin-like growth factor-binding protein 7 in the sample as compared to a first predetermined threshold, wherein the insulin-like growth factor-binding protein 7 comprises amino acid residues 27-282 of SEQ ID NO: 1, wherein the first predetermined threshold comprises a predetermined level of concentration of urinary insulin-like growth factor-binding protein 7;
(c) measuring a level or concentration of metalloproteinase inhibitor 2 in the sample as compared to a second predetermined threshold, wherein the metalloproteinase inhibitor 2 comprises amino acid residues 27-220 of SEQ ID NO: 3, wherein the second predetermined threshold comprises a predetermined level or concentration of the metalloproteinase inhibitor 2;
(d) identifying the subject at risk for occurrence of RIFLE I or F within 24 hours of the time at which the urine sample is obtained from the subject when the level of insulin-like growth factor-binding protein 7 in the sample is elevated as compared to the first predetermined threshold and the level of metalloproteinase inhibitor 2 in the sample is elevated as compared to the second predetermined threshold; and
(e) treating the identified subject of (e), wherein the treating comprises initiating kidney replacement therapy, withdrawing delivery of compounds known to be damaging to the kidney, kidney transplant, or modifying diuretic administration.

14. The method of claim 13, comprising measuring the concentration of insulin-like growth factor-binding protein 7 and metalloproteinase inhibitor 2 in the sample.

15. The method of claim 13, wherein sepsis is severe sepsis or septic shock.

16. The method of claim 13, wherein measuring the level or concentration of insulin-like growth factor-binding protein 7 comprises contacting all or a portion of the urine sample with a first binding reagent which specifically binds to the insulin-like growth factor-binding protein 7, and generating a first assay result indicative of the level or concentration the insulin-like growth factor-binding protein 7, and wherein measuring the level or concentration of metalloproteinase inhibitor 2 comprises contacting all or a portion of the urine sample with a second binding reagent which specifically binds to metalloproteinase inhibitor 2, and generating a second assay result indicative of the level or concentration of the metalloproteinase inhibitor 2 to the second binding reagent.

17. The method of claim 16, further comprising combining the first and second assay result using a function that converts the first and second assay result into a single combined assay result.

18. The method of claim 13, wherein the risk for occurrence of RIFLE I or F acute kidney injury is within 12 hours of the time at which urine sample is obtained.

19. The method of claim 1, wherein the metalloproteinase inhibitor 2 comprises amino acid residues 27-220 of SEQ ID NO: 3.

20. The method of claim 1, wherein the insulin-like growth factor-binding protein 7 consists of amino acid residues 27-282 of SEQ ID NO: 1.

21. The method of claim 20, wherein the metalloproteinase inhibitor 2 consists of amino acid residues 27-220 of SEQ ID NO: 3.

* * * * *

UNITED STATES PATENT AND TRADEMARK OFFICE
CERTIFICATE OF CORRECTION

| | | |
|---|---|---|
| PATENT NO. | : 10,935,548 B2 | Page 1 of 1 |
| APPLICATION NO. | : 14/363724 | |
| DATED | : March 2, 2021 | |
| INVENTOR(S) | : Joseph Anderberg et al. | |

It is certified that error appears in the above-identified patent and that said Letters Patent is hereby corrected as shown below:

In the Claims

Claim 6, Column 90, Lines 9-10, the text "or concentration of the metalloproteinase inhibitor 2 to the second binding reagent." should be changed to --or concentration of the metalloproteinase inhibitor 2.--

Claim 13, Column 90, Line 41, the text "mined level of concentration of urinary insulin-like" should be changed to --mined level or concentration of urinary insulin-like--

Claim 13, Column 90, Line 58, the text "(e) treating the identified subject of (e), wherein the" should be changed to --(e) treating the identified subject of (d), wherein the--

Claim 16, Column 91, Line 7, the text "concentration the insulin-like growth factor-binding protein" should be changed to --concentration of the insulin-like growth factor-binding protein--

Claim 16, Column 91, Lines 13-14, the text "or concentration of the metalloproteinase inhibitor 2 to the second binding reagent." should be changed to --or concentration of the metalloproteinase inhibitor 2.--

Signed and Sealed this
Twenty-second Day of June, 2021

Drew Hirshfeld
*Performing the Functions and Duties of the
Under Secretary of Commerce for Intellectual Property and
Director of the United States Patent and Trademark Office*